US010112993B2

(12) United States Patent
Kuijpers et al.

(10) Patent No.: US 10,112,993 B2
(45) Date of Patent: Oct. 30, 2018

(54) FACTOR H POTENTIATING ANTIBODIES AND USES THEREOF

(71) Applicant: Stichting Sanquin Bloedvoorziening, Amsterdam (NL)

(72) Inventors: Taco Willem Kuijpers, Amsterdam (NL); Diana Wouters, Amsterdam (NL); Maria Clara Brouwer, Amsterdam (NL); Richard Benjamin Pouw, Amsterdam (NL)

(73) Assignee: STICHTING SANQUIN BLOEDVOORZIENING, Amsterdam (NL)

( * ) Notice: Subject to any disclaimer, the term of this patent is extended or adjusted under 35 U.S.C. 154(b) by 68 days.

(21) Appl. No.: 15/504,983

(22) PCT Filed: Aug. 20, 2015

(86) PCT No.: PCT/NL2015/050584
§ 371 (c)(1),
(2) Date: Feb. 17, 2017

(87) PCT Pub. No.: WO2016/028150
PCT Pub. Date: Feb. 25, 2016

(65) Prior Publication Data
US 2017/0355753 A1 Dec. 14, 2017

(30) Foreign Application Priority Data
Aug. 20, 2014 (EP) ..................... 14181631

(51) Int. Cl.
*C07K 16/18* (2006.01)
*A61K 39/395* (2006.01)
*C07K 16/36* (2006.01)

(52) U.S. Cl.
CPC .............. *C07K 16/18* (2013.01); *C07K 16/36* (2013.01); *A61K 39/3955* (2013.01); *C07K 2317/34* (2013.01); *C07K 2317/51* (2013.01); *C07K 2317/515* (2013.01); *C07K 2317/54* (2013.01); *C07K 2317/55* (2013.01); *C07K 2317/56* (2013.01); *C07K 2317/565* (2013.01); *C07K 2317/75* (2013.01); *C07K 2317/76* (2013.01)

(58) Field of Classification Search
CPC ............................ C07K 16/18; C07K 2317/34; C07K 2317/51; C07K 2317/515; C07K 2317/54; C07K 2317/56; C07K 2317/565; C07K 2317/55; C07K 2317/76; A61K 39/3955
See application file for complete search history.

(56) References Cited

U.S. PATENT DOCUMENTS

2016/0279221 A1* 9/2016 Dutta ................... C07K 16/205
2016/0297892 A1* 10/2016 Heibroch Petersen ......................
C07K 16/36

FOREIGN PATENT DOCUMENTS

WO  WO 2006/012621  2/2006
WO  WO 2007/066017  6/2007
WO  WO 2014/055835  4/2014

OTHER PUBLICATIONS

International Search Report dated Jan. 28, 2016 for Appln. No. PCT/NL2015/050584.
Morgan et al., "Structural basis for engagement by complement factor H of C3b on a self surface", Nature Structural & Molecular Biology, vol. 18, No. 4, Apr. 2011, Published online Feb. 13, 2011, pp. 463-471.
Corey et al., "Mechanistic Studies of the Effects of Anti-factor H Antibodies on Complement-mediated Lysis", The Journal of Biological Chemistry, vol. 275, No. 17, Apr. 28, 2000, pp. 12917-12925.
Cheng et al., "Complement Factor H as a Marker for Detection of Bladder Cancer", Clinical Chemistry, 51, No. 5, 2005, pp. 856-863.
Takahashi et al., "Mouse anti-human B7-H3 antibody M30 light chain variable region cDNA", Nov. 1, 2012, pp. 1-2, ibis.internal. epo.org/exam/dbfetch.jsp?id=GSN:BAE70904 (NPL reference No. XP002738082).
Lydon, "Anti-LTA mAb light chain variable region, SEQ ID: 60", Jun. 27, 2013, pp. 1-2, ibis.internal.epo.org/exam/dbfetch.jsp?id=GSP:BAQ13707 (NPL reference No. XP002738080).
Gearing, "Mouse anti-CD20 heavy chain variable domain, SEQ ID 19", Apr. 18, 2013, pp. 1-2, ibis.internal.epo.org/exam/dbfetch.jsp?id=GSP:BAN36074 (NPL reference No. XP002738081).

* cited by examiner

*Primary Examiner* — Kimberly Ballard
(74) *Attorney, Agent, or Firm* — Pillsbury Winthrop Shaw Pittman, LLP

(57) ABSTRACT

The invention relates to isolated, synthetic or recombinant antibodies and fragments thereof specific for factor H. The invention further relates to the use of such antibodies and fragments for inhibiting complement activation and treatment of disorders associated with complement activation.

16 Claims, 8 Drawing Sheets

Specification includes a Sequence Listing.

A

B

A

B

C

A

B

C

A

B

C

D

SEQUENCE LISTING

<160> NUMBER OF SEQ ID NOS: 16

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Light
      chain CDR1-IMGT

<400> SEQUENCE: 1

Ser Ser Val Lys Tyr
1               5

<210> SEQ ID NO 2
<211> LENGTH: 3
<212> TYPE: PRT
<213> ORGANISM: Artificial Sequence
<220> FEATURE:
<223> OTHER INFORMATION: Description of Artificial Sequence: Light
      chain CDR2-IMGT

<400> SEQUENCE: 2

Ala Thr Ser
1

<210> SEQ ID NO 3

```
<211> LENGTH: 9
<212> TYPE: PRT
<213> ORGANISM: Artificial Sequence
<220> FEATURE:
<223> OTHER INFORMATION: Description of Artificial Sequence: Light
      chain CDR3-IMGT

<400> SEQUENCE: 3

Gln Gln Trp Ser Ile Ile Pro Pro Thr
1               5

<210> SEQ ID NO 4
<211> LENGTH: 105
<212> TYPE: PRT
<213> ORGANISM: Artificial Sequence
<220> FEATURE:
<223> OTHER INFORMATION: Description of Artificial Sequence: Light
      chain variable region V-D-J-Region-IMGT

<400> SEQUENCE: 4

Ile Val Leu Ser Gln Ser Pro Thr Phe Leu Ser Ala Ser Pro Gly Glu
1               5                   10                  15

Lys Val Thr Val Thr Cys Arg Ala Ser Ser Ser Val Lys Tyr Met His
            20                  25                  30

Trp Tyr Gln Gln Lys Pro Gly Ala Ser Pro Lys Pro Trp Ile Phe Ala
        35                  40                  45

Thr Ser Asn Leu Ala Ser Gly Val Pro Ala Arg Phe Ser Gly Ser Gly
    50                  55                  60

Ser Gly Thr Ser Tyr Ser Leu Thr Ile Ser Arg Val Glu Ala Glu Asp
65                  70                  75                  80

Ala Ala Thr Tyr Tyr Cys Gln Gln Trp Ser Ile Ile Pro Pro Thr Phe
                85                  90                  95

Gly Asn Gly Thr Lys Leu Glu Leu Lys
            100                 105

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Heavy chain
      CDR1-IMGT

<400> SEQUENCE: 5

Asp Phe Ser Leu Ala Arg Tyr Gly
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Heavy chain
      CDR2-IMGT

<400> SEQUENCE: 6

Ile Trp Ser Gly Gly Thr Ala
1               5

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Heavy chain
```

CDR3-IMGT

<400> SEQUENCE: 7

Ala Arg Asn Phe Gly Asn Tyr Ala Val Asp Tyr
1               5                   10

<210> SEQ ID NO 8
<211> LENGTH: 112
<212> TYPE: PRT
<213> ORGANISM: Artificial Sequence
<220> FEATURE:
<223> OTHER INFORMATION: Description of Artificial Sequence: Heavy chain
      variable region V-D-J-Region-IMGT

<400> SEQUENCE: 8

Gln Val Gln Leu Gln Gln Ser Gly Pro Gly Leu Val Gln Pro Ser Gln
1               5                   10                  15

Ser Leu Ser Ile Thr Cys Thr Val Ser Asp Phe Ser Leu Ala Arg Tyr
            20                  25                  30

Gly Val His Trp Ile Arg Gln Ser Pro Gly Lys Gly Leu Glu Trp Leu
        35                  40                  45

Gly Val Ile Trp Ser Gly Gly Thr Ala Asp Tyr Asn Ala Ala Phe Ile
    50                  55                  60

Ser Arg Leu Asn Ile Asn Lys Asp Asn Ser Lys Ser Gln Val Phe Phe
65                  70                  75                  80

Lys Met Asn Ser Leu Gln Ala Asn Asp Thr Ala Ile Tyr Tyr Cys Ala
                85                  90                  95

Arg Asn Phe Gly Asn Tyr Ala Val Asp Tyr Trp Gly Gln Gly Thr Ser
            100                 105                 110

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence: Light chain
      CDR1-IMGT

<400> SEQUENCE: 9
tcaagtgtca aatac                                                    15

<210> SEQ ID NO 10
<211> LENGTH: 9
<212> TYPE: DNA
<213> ORGANISM: Artificial Sequence
<220> FEATURE:
<223> OTHER INFORMATION: Description of Artificial Sequence: Light chain
      CDR2-IMGT

<400> SEQUENCE: 10 gccacatcc                                                            9

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Light chain
      CDR3-IMGT

<400> SEQUENCE: 11
cagcagtgga gtattatccc acccacg                                       27

-continued

<210> SEQ ID NO 12
<211> LENGTH: 319
<212> TYPE: DNA
<213> ORGANISM: Artificial Sequence
<220> FEATURE:
<223> OTHER INFORMATION: Description of Artificial Sequence: Light chain
      variable region V-D-J-Region-IMGT

<400> SEQUENCE: 12
caaattgttc tctcccagtc tccaacattc ctgtctgcat ctccaggtga aaggtcaca      60 gtgacttgca gggccagttc aagtgtcaaa tacatgcact ggtatcagca gaaaccagga    120
gcctccccca aaccctggat ttttgccaca tccaacctgg cttctggagt ccctgctcgc    180
ttcagtggca gtgggtctgg gacctcttat tctctcacaa tcagcagagt ggaggctgaa    240
gatgctgcca cttattactg ccagcagtgg agtattatcc cacccacgtt cggtaatggg    300
accaagctgg agctgaaac                                                 319

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Heavy chain
      CDR1-IMGT

<400> SEQUENCE: 13
gatttctcat tagctaggta tggt                                            24

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Heavy chain
      CDR2-IMGT

<400> SEQUENCE: 14
atatggagtg gtggaaccgc a                                               21

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence: Heavy chain
      CDR3-IMGT

<400> SEQUENCE: 15
gccagaaatt ttggtaacta cgctgtggac tac                                  33

<210> SEQ ID NO 16
<211> LENGTH: 337
<212> TYPE: DNA
<213> ORGANISM: Artificial Sequence
<220> FEATURE:
<223> OTHER INFORMATION: Description of Artificial Sequence: Heavy chain
      variable region V-D-J-Region-IMGT

<400> SEQUENCE: 16
caggtgcagc tgcagcagtc aggacctggc ctagtgcagc cctctcagag cctgtccatt     60
acctgcacag tctctgattt ctcattagct aggtatggtg tacactggat tcgccagtct    120

```
ccaggaaagg gtctggagtg gctgggagtg atatggagtg gtggaaccgc agactataat        180
gcagctttca tatccagact gaacatcaac aaggacaatt ccaagagcca agttttcttt        240
aaaatgaaca gtctccaagc taatgacaca gccatatatt actgtgccag aaattttggt        300
aactacgctg tggactactg gggtcaagga acctcag                                337
```

FACTOR H POTENTIATING ANTIBODIES AND USES THEREOF

CROSS-REFERENCE TO RELATED APPLICATIONS

This is the U.S. National Stage of PCT/NL2015/050584, filed Aug. 20, 2015, which in turn claims priority to European Application No. 14181631.4, filed Aug. 20, 2014, the entire contents of both applications being incorporated herein by reference in their entireties.

The invention relates to the field of immunology and medicine. In particular, the invention relates to factor H specific antibodies and uses thereof.

The complement system is an important element of innate immunity that contributes to the protection of many organisms such as mammals against invading pathogens. The complement system consists of over 30 different components which are mainly synthesized in the liver. Activation of the complement system occurs by three different pathways, the classical pathway, the lectin pathway and the alternative pathway. The three pathways converge at the formation of a C3 convertase, which are different for each pathway but have similar activity.

In the classical complement pathway, activation of the complement component (C) 1 complex, consisting of C1q, C1r and C1s, occurs upon binding to antibody-antigen complexes. The C1 complex cleaves C4 and C2 leading to the formation of a C3 convertase consisting of C4bC2a. The C3 convertase cleaves C3 into the active components C3a and C3b. In the lectin pathway, mannose binding lectin binds to mannose residues on pathogenic surfaces which activates serine proteases MASP-1 and MASP-2 that are able to cleave C4 and C2. As in the classical pathway, this leads to the formation of the C4bC2a C3 convertase. This C3 convertase can bind C3b to form a C5 convertase. Contrary to the classical and lectin pathways, the alternative pathway has a low level of continuous activity due to spontaneous hydrolysis of C3 to C3 ($H_2O$) in plasma. This C3b-like C3 ($H_2O$) can form a fluid phase C3 convertase by binding factor B (FB) which in turn is activated into Bb by factor D. Similarly, when C3b binds to a surface, it may bind FB to form C3bB. This complex is cleaved by factor D to C3bBb which is the C3 convertase of the alternative pathway that can be stabilized by properdin (factor P) to C3bBbP. This C3 convertase is able to cleave C3 into C3a and C3b. In addition to this process the alternative pathway acts as amplification loop for the classical and lectin activation pathways as C3b generated in these pathways may act as starting point for the alternative pathway. Thereby, the amplification loop results in a reinforcement of the classical and lectin pathway. The C3 convertase formed in one of the three activation pathways can bind C3b to form a C5 convertase. The C5 convertases of all three complement pathways activate C5 into C5a and C5b which initiates the terminal pathway of the complement system. C5b binds C6, C7, C8 and C9 to form the membrane attack complex (MAC) which forms a transmembrane channel and causes cell lysis.

Next to forming a pore in the membrane of pathogens, complement helps clearing pathogens or altered self-cells by opsonisation with C3b molecules and production of pro-inflammatory peptides such as C3a and C5a that attract and activate immune cells to the site of infection. Because of the strong pro-inflammatory nature of complement, host cells are well protected by several membrane and soluble complement-regulating proteins.

The alternative pathway contributes for 80-90% to total complement activity. Regulation of this pathway is therefore crucial. C3 ($H_2O$) that is formed by spontaneous hydrolysis of C3, and C3b are generally, if not bound by a pathogen, rapidly inactivated by factor H (FH), factor I (FI) and host cell surface molecules thereby inhibiting the formation of the C3 convertases. CD55 (also termed decay accelerating factor or DAF) binds C3b at the host cell surface. FI cleaves C3b to an inactive form but is dependent on co-factors either expressed on cell surfaces (CD46, MCP) or circulating in plasma (FH). FH is a plasma glycoprotein that is essential for controlling the alternative pathway of complement both in solution and on cell surfaces. FH binds C3b at the same position as FB, thereby preventing the formation of C3 convertases. FH also has decay accelerating activity, i.e. it promotes the dissociation of alternative pathway C3 convertases once they have been formed. Whether FH binds to C3b is determined by the carbohydrates present on the cell surface. Sialic acid, glycosaminoglycans and heparin present on the host cell surface promotes binding of FH to C3b, whereas binding of C3b to molecules expressed on the surface of pathogens results in binding of FB. FH thus exerts its complement inhibitory activity on host cells but not on the surface of pathogenic cells because the cell surface molecules that bind FH are expressed on host cells but generally not on pathogenic cells.

FH deficiency or impaired recognition of host surfaces due to mutations is associated with complement-mediated tissue damage and disease. Next to controlling complement activation during normal hemostasis, FH also plays an important role in limiting complement mediated damage of diseased cells and tissues. Multiple mutations in the FH gene have been described that may lead to loss of function of the FH protein. The C-terminal region of FH is a hotspot for mutations in disease. This is a critical region for binding of FH to host cells. Most disease-associated mutations in this region interfere with FH binding. Most patients with a mutated FH gene have heterozygous mutations, meaning that approximately half of the circulating FH has normal function. However, this apparently is not sufficient to protect self surfaces in certain conditions in which complement is activated. FH deficiency may lead to kidney disease such as membranoproliferative glomerulenephritis (MPGN) and atypical hemolytic uremic syndrome (aHUS). More recently a relationship has been described between FH mutations and age-related macular disease (AMD).

Currently the standard treatment for FH deficiency, such as in aHUS, is plasma supplementation or plasma exchange therapy. With such therapy deficient complement regulators are supplemented. Plasma exchange therapy in addition removes mutant complement factors and/or autoantibodies directed against complement factors. However, plasma therapy also has some limitations. No prospective clinical studies have shown that plasma exchange therapy is safe or effective in treating aHUS and efficiency of plasma therapy may depend on the underlying mutations. Some patients develop anaphylactic reactions to fresh frozen plasma, which may require cessation of any form of plasma therapy. Moreover, plasma exchange may worsen the clinical picture of aHUS due to the administration of plasma-derived active pathogenic complement components.

Recently the therapeutic monoclonal antibody eculizumab has been approved for treatment of aHUS and paroxysmal nocturnal hemoglobinuria (PNH) in several countries, among which the US and European countries. Eculizumab is a humanized mouse monoclonal antibody specific for C5 that prevents cleavage of C5 to C5a and C5b.

It thus prevents activation of the terminal pathway and decreases the influx of immune cells. However, the use of eculizumab is associated with unwanted side effects. As it blocks C5, which is a crucial component for the initiation of the terminal pathway, patients treated with eculizumab become vulnerable to infection with encapsulated bacteria (such as *Neisseria meningitidis*), the clearance of which is very dependent on MAC formation. Therefore, vaccination against the meningococcus is required for patients prior to receiving treatment with eculizumab. Further, since eculizumab acts downstream of C3, C3 deposition is maintained, which is detrimental in several disorders involving unwanted or excessive complement activation. In addition, high costs are involved with eculizumab treatment and the availability of the antibody is limited.

A mouse monoclonal antibody that binds CCP18 is described by Cheng et al. (Clinical Chemistry, 2005). It is described that this antibody, called X52.1, increases binding of FH to C3b and C3d which is thought to be caused by dimerization of FH. The increased binding of FH to C3b and C3d induced by X52.1 results in an increased complement mediated lysis of cells, including RBCs and several types of cancer cells as shown by Corey et al. (J Biol Chem. 2000). This demonstrates that antibody X52.1 inhibits the complement inhibitory activity of FH. Indeed, Corey et al. suggests that the antibody can be used in the treatment of cancer by enhancing complement-mediated lysis of cancer cells.

In view of the above, there is thus a need for improved therapy of disorders associated with unwanted or excessive complement activation.

It is an object of the present invention to provide a treatment strategy for disorders associated with unwanted or excessive activation of the alternative pathway of the complement system that overcomes the shortcomings of current treatment strategies for such disorders. It is a further object of the invention to provide antibodies that can be used in the treatment of such disorders that have improved properties over currently available antibodies. The antibodies and fragments thereof of the invention are specific for FH and potentiate the function of FH thereby specifically inhibiting the activation of the alternative complement pathway.

The invention provides an isolated, synthetic or recombinant antibody or fragment thereof that specifically binds to complement control protein domain 17 (CCP17) and/or CCP18 of factor H (FH) and potentiates FH activity.

The present inventors for the first time developed and isolated an antibody that is capable of specifically binding FH that is capable of potentiating the function of FH. The potentiating anti-FH antibodies of the invention are potent inhibitors of activation of the alternative complement pathway. Without wishing to be bound by theory, this potentiation is thought to be independent of multimerization of FH molecules by the antibody. As demonstrated in the Examples, anti-FH potentiating antibodies inhibit or even completely block lysis of red blood cells incubated with healthy human donor serum. Under normal conditions, incubation of sheep red blood cells (SRBCs) with healthy human donor serum does not lead to lysis of the SRBCs, because they are protected by factor H in the serum that binds to sialic acid on the SRBC surface. Upon incubation of normal human serum with a monoclonal antibody blocking the function of FH, lysis of SRBCs is observed. This can be explained by insufficient protection of the cell surface by serum FH. This lysis induced by an anti-FH blocking antibody is inhibited or even blocked by the –FH potentiating antibodies of the present invention. The Examples further show that the potentiating anti-FH antibodies of the invention inhibit alternative pathway mediated C3 deposition on zymosan and lipopolysaccharide (LPS). It was further found that the potentiating anti-FH antibody restores the protective function of FH in serum from 3, unrelated, aHUS patients. As further demonstrated in the Examples, lysis of red blood cells incubated in the presence of serum of an aHUS patient was completely abolished when the serum was pre-incubated with the potentiating anti-FH antibodies of the invention.

The Examples further demonstrate that not only the intact anti-FH antibodies potentiate the function of FH. The same effect is observed for Fab' and F(ab')$_2$ fragments of such antibodies. Since Fab' cannot crosslink FH molecules, the potentiating effect of the antibody and antibody fragments can not be the result of such crosslinking. The Examples, however, do demonstrate that the anti-FH antibodies and fragments thereof are able to inhibit C3 deposition, suggesting that the tested fragments are able to increase binding of FH to C3b, iC3b and C3d. Without being bound by theory it is therefore believed that binding of the potentiating anti-FH antibody to FH causes a conformational change of FH that results in an increase of binding of FH to C3b, iC3b and C3d on the surface of cells.

The potentiating anti-FH antibodies and fragments according to the invention are highly preferred over anti-05 antibodies such as eculizumab for inhibiting unwanted or excessive activation of the alternative pathway of the complement system. The main advantages are that the complement inhibitory effect of the antibodies and fragments of the invention interferes with complement activation at the level of activated C3 instead of C5 and that this interference occurs by enhancing a naturally occurring inhibitor. As a result, only interference with C3 only occurs when C3 is activated. On the contrary, with general C3-inhibitors all circulating C3 is blocked which may lead to general C3 deficiency. Although C3, like C5 which is the target of eculizumab, is involved in all three pathways of the complement system, FH specifically inhibits the amplification loop of the alternative pathway wherein the cleavage of C3 into C3b and subsequent binding thereof to FB at the cell surface and formation of the C3 convertase promotes cleavage of further C3 molecules into C3b. The main advantage of the fact that the antibodies and fragments of the invention interfere with complement activation at the level of C3 is that accumulation of C3b on the surface and release of C3a is avoided. Contrary, if complement activation is inhibited at the C5 level, such as with eculizumab, accumulation of C3b and release of C3a is not inhibited. C3b acts as an opsonin and C3a is an anaphylatoxin. Accumulation of C3b and C3a formation is thus preferably prevented, because these processes result in the attraction of immune cells and opsonophagocytosis of the target. This means that for instance PNH patients receiving eculizumab still need transfusions because accumulation of C3b results in opsonisation of red blood cells, which are subsequently removed in the liver and spleen. Further, treatment with anti-05 antibodies results in accumulation of C3b and C3a formation on cells that would otherwise be lysed by the MAC. An important disadvantage of anti-05 antibodies is that patients become vulnerable for infections because the antibodies interfere with complement activation induced by pathogens as well. By targeting a regulator of the complement system that protects host cells, this is avoided.

The term "antibody" as used herein, refers to an immunoglobulin protein comprising at least a heavy chain variable region (VH), paired with a light chain variable region (VL), that is specific for a target epitope. The term covers both polyclonal and monoclonal antibodies. It refers to any form of antibody that specifically binds to CCP17 and/or CCP18, preferably to CCP18, of FH, including full length immunoglobulins. An antibody or fragment thereof according to the invention comprises at least one antigen binding site. The term "antigen binding site" as used herein refers to a site of an antibody or fragment thereof comprising at least one CDR sequence, preferably at least two CDR sequences, more preferably at least three CDR sequences. For instance, an antigen binding site comprises light chain CDRs 1-3 or heavy chain CDRs 1-3. A particularly preferred antigen binding site comprises light chain CDRs 1-3 and heavy chain CDRs 1-3. A "fragment of an antibody" is defined herein as a part that has at least one shared property as said antibody in kind, not necessarily in amount. A fragment is capable of specifically binding the same antigen as said antibody, i.e. CCP17 and/or CCP18 of FH, albeit not necessarily to the same extent. A fragment of an antibody comprises at least one CDR sequence of said antibody. Said fragment preferably comprises the heavy chain CDR1, CDR2 and CDR3 sequences of an antibody, as well as the light chain CDR1, CDR2 and CDR3 sequence of said antibody. Non-limiting examples of a fragment of an antibody are a single domain antibody, a single chain antibody, a nanobody, an unibody, a single chain variable fragment (scFv), a Fab fragment, a Fab' fragment, a $F(ab')_2$ fragment and a $F(ab)_2$ fragment. A preferred fragment of an antibody comprises at least a heavy chain variable domain (VH) and/or a light chain variable domain (VL). A more preferred fragment comprises at least a Fab fragment. As demonstrated in the Examples, Fab' fragments of potentiating anti-FH antibodies of the invention retain the ability to potentiate the function of FH. Particularly preferred fragments are a Fab fragment, a Fab' fragment, a $F(ab')_2$ fragment and a $F(ab)_2$ fragment of antibodies according to the invention.

As is well known by the skilled person, antibodies contain two heavy chains and two light chains. A heavy chain of an antibody is the larger of the two types of chains making up an immunoglobulin molecule. A heavy chain comprises a constant domain and a variable domain, which variable domain is involved in antigen binding. A light chain of an antibody is the smaller of the two types of chains making up an immunoglobulin molecule. A light chain comprises a constant domain and a variable domain. The variable domain of the light chain is often, but not always, together with the variable domain of the heavy chain involved in antigen binding. Complementary-determining regions (CDRs) are the hypervariable regions present in heavy chain variable domains and light chain variable domains. In case of full length antibodies, the CDRs 1-3 of a heavy chain and the CDRs 1-3 of the connected light chain together form the antigen-binding site.

The percentage of identity of an amino acid sequence or nucleic acid sequence, or the term "% sequence identity", is defined herein as the percentage of residues of the full length of an amino acid sequence or nucleic acid sequence that is identical with the residues in a reference amino acid sequence or nucleic acid sequence after aligning the two sequences and introducing gaps, if necessary, to achieve the maximum percent identity. Methods and computer programs for the alignment are well known in the art, for example "Align 2".

Antibodies and fragments according to the invention specifically bind CCP17 and/or CCP18 of FH. Preferred antibodies and fragments at least bind CCP18 of FH. FH is a 155 kilodalton (kDa) soluble glycoprotein that circulates in plasma. FH contains 20 complement control protein (CCP) domains, numbered 1-20 starting at the N-terminus of FH. The CCP domains are also referred to as short consensus repeats (SCR) or sushi domains. CCPs 1-4 are domains involved in regulation and CCPs 19-20 are involved in binding C3b and CCP s 6, 7, 8, 19 and 20 bind to GAGs and sialic acid expressed at the surface of cells. Antibodies that bind CCP19 and/or CCP20 inhibit activity of FH. Without being bound by theory, it is believed that antibodies that bind domains located adjacent to binding domains CCP19 and CCP20, i.e. CCP17 and CCP18, potentiate the activity of FH. Indeed, as demonstrated in the Examples an antibody that binds CCP18 potentiates the function of FH. As used herein the terms "specific for" and "specifically binds" or "capable of specifically binding" refer to the non-covalent interaction between an antibody and its epitope. It indicates that the antibody or fragment preferentially binds to said epitope over other epitopes or other antigens. Hence, although the antibody or fragment may non-specifically bind to other epitopes or antigens, the binding affinity of said antibody or fragment for its epitope is significantly higher than the binding affinity of said antibody or fragment for any other epitope or antigen.

Antibodies and fragments according to the invention are able to potentiate the activity of FH, preferably of human FH. With the term "potentiating FH activity" is meant that the activity of FH is increased if an antibody or fragment according to the invention binds to FH. Although antibodies that specifically bind FH are known, these antibodies are predominantly used for the detection of FH, for instance in immunoassay's. Further, antibodies specific for FH have been described that block or inhibit its function. The present inventors for the first time developed an FH-specific antibody that, upon binding FH, potentiates its function. It was surprisingly found that the activity of potentiating anti-FH antibodies of the invention increase the complement inhibiting activity of FH. Said FH activity can be potentiated in vitro or in vivo. The activity of FH that is potentiated by antibodies and fragments of the invention is preferably inhibition of alternative complement activation, preferably in an individual. As used herein the term "alternative complement activation" refers to activation of the complement system via the alternative pathway, i.e. involving at least the formation of the C3 convertase of the alternative pathway, i.e. C3bBb/C3bBbP, or involving an increase in the formation of this C3 convertase. Alternative complement activation may further involve cleavage of C3 into C3a and C3b by the alternative pathway C3 convertase, formation of the alternative pathway C5 convertase, i.e. C3bBbC3b/C3bBbC3b, and/or cleavage of C5 and subsequent binding of C6, C7, C8 and C9 to form the MAC. Alternative complement activation may further include an increase in the alternative pathway amplification loop. Said alternative complement activation is preferably inhibited in an individual, preferably in a bodily fluid of an individual, preferably in blood, interstitial fluid or cerebrospinal fluid, more preferably in blood. As used herein, an "individual" is a human or an animal that comprises a complement system as part of its immune system. Preferably said individual is a mammal, more preferably a human.

As used herein "inhibition of alternative complement activation" comprises any alteration in the amount or activity of a component, factor or activity of the alternative complement system that causes or is the result of inhibition thereof. Inhibition of alternative complement activation for instance comprises an inhibition of hemolytic activity, an inhibition of complement component 3 (C3) deposition on cells of said individual, an increase of binding of FH to C3b, iC3b and/or C3d, an inhibition of the formation of the alternative complement pathway C3 convertase C3bBb/C3bBbP, an inhibition of binding of factor B to C3b and/or inhibition of the interaction between C3b and factor B, an inhibition of the cleavage of C3 into C3a and C3b by the alternative pathway C3 convertase, an increase in the binding of fH to host cells, in particular to sialic acid, glycosaminoglycans and/or heparin expressed on host cells, an inhibition of the amplification loop of the alternative complement pathway, and inhibition of the formation of the alternative complement pathway C5 convertase C3bBbC3bP/C3bBbC3bP, an inhibition of the cleavage of C5 to C5a and C5b by the alternative pathway C5 convertase, an increase in the decay accelerating activity of FH, i.e. promotion of the dissociation of alternative pathway C3 convertases once they have formed, and/or an increase in FI co-factor activity resulting in degradation of C3b. Inhibition of alternative complement activation by FH that is potentiated by the anti-FH antibodies and fragments of the invention preferably comprises an inhibition of hemolytic activity, an inhibition of C3 deposition on cells of said individual, and/or an increase of binding of FH to C3b, iC3b and/or C3d.

"Inhibition" as used herein preferably means that the indicated activity is reduced by at least about 25%, more preferably at least about 50%, more preferably at least about 75%, more preferably at least about 80%, more preferably at least about 85%, more preferably at least about 90%, most preferably at least about 95%. Thus, "inhibition of alternative complement activation" preferably means that the activity of the alternative complement pathway is reduced by at least about 25%, more preferably at least about 50%, 75%, 80%, 85%, 90% or 95%. Similarly, "an inhibition of hemolytic activity" preferably means that hemolytic activity is reduced by at least about 25%, more preferably at least about 50%, 75%, 80%, 85%, 90% or 95%.

"Increase" as used herein preferably means that the indicated activity is increased by at least about 25%, more preferably at least about 50%, more preferably at least about 75%, more preferably at least about 80%, more preferably at least about 85%, more preferably at least about 90%, most preferably at least about 95%. Thus, "an increase of binding of FH to C3b" preferably means that the binding of FH to C3b is increased by at least about 25%, more preferably at least about 50%, 75%, 80%, 85%, 90% or 95%. Similarly, "an increase in binding of FH to host cells" preferably means that binding of FH to host cells is increased by at least about 25%, more preferably at least about 50%, 75%, 80%, 85%, 90% or 95%.

As used herein "hemolytic activity" refers to the rupture of red blood cells and the subsequent release of the cell's content into e.g. the circulation induced by activation of the complement system, preferably as a result of the formation of MAC at the cell surface. Hemolytic activity is for instance measured as described herein in the Examples by using a hemolytic assay as described by Sanchez-Corral et al. (2004) and Wouters et al. (2008), optionally with some modifications. In this assay, red blood cells such as sheep red blood cells (SRBCs) are incubated with serum, e.g. human serum, e.g. at 37° C. for 1.25 hours while shaking. Sera with low levels of FH or dysfunctional FH lead to lysis of the SRBCsLysis can stopped by addition of veronal buffer containing 20 mM EDTA followed by centrifugation in a pre-chilled centrifuge (e.g. 7° C.) for 2.5 minutes. The percentage of red blood cell lysis is determined by measuring the absorbance of the supernatants was measured at 412 nm. The serum can for instance be from healthy human individuals or from human individuals suffering from a disorder associated with unwanted or excessive alternative pathway complement activation, such as aHUS. The ability of an antibody or fragment to inhibit hemolytic activity can be determined by incubating the red blood cells with serum in the presence of the antibody or fragment.

Inhibition of C3 deposition is for instance measured using a C3 deposition assay as described herein in the Examples. This assay involves the coating of microtiterplates with either zymosan or LPS. The plates are subsequently incubated with serum, e.g. from healthy individuals or from individuals suffering from a disorder associated with unwanted or excessive alternative complement activation as indicated above, in the presence or absence of antibody or fragments. C3 deposition on zymosan or LPS can be detected with an anti-C3 antibody.

An increase of binding of FH to C3b is for instance measured using a ELISA as described herein in the Examples. This assay involves coating of microtiter ELISA plate with C3b and incubation of the plate with serum, e.g. from healthy individuals or from individuals suffering from a disorder associated with unwanted or excessive alternative complement activation as indicated above. Bound FH can be detected with an anti-FH antibody, such as peroxidase-labeled polyclonal anti-FH. The ability of an antibody or fragment to enhance FH binding to C3b can be determined by preincubating the serum in the presence of the antibody or fragment before incubation with the coated C3b. As another example, binding of FH to C3b can be determined using Surface Plasmon Resonance (SPR). SPR is a technique to measure biomolecular interactions in real-time in a label free environment. One of the interactants, for instance C3b, is immobilized to a sensor surface, and the other, for instance FH, is free in solution and passed over the surface, e.g. in the presence or absence of (different concentrations of) an antibody or fragment of the invention.

Antibodies or fragments thereof according to the invention are preferably monoclonal antibodies or fragments. A monoclonal antibody is an antibody consisting of a single molecular species. Monoclonal antibodies can be advantageously produced recombinantly so that amounts of the antibody can be obtained that are significantly higher than that of polyclonal antibodies present in an antiserum. However, polyclonal antibodies and fragments are also encompassed by the invention. An antibody or fragment according to the present invention preferably is a chimeric or humanized antibody. Said antibody or fragment thus preferably comprises at least human light chain and heavy chain constant regions. More preferably said antibody or fragment also comprises human framework regions in the heavy and light chain variable regions. Further preferred are human antibodies or fragments, which consist entirely of human sequences. The use of chimeric, humanized or human antibodies is preferred over the use of non-human antibodies because the use of non-human antibodies or fragments for treatment of human diseases is hampered by a number of factors. The human body may recognize non-human antibodies as foreign, which will result in an immune response against the non-human antibodies or fragments, resulting in adverse side effects and/or rapid clearance of the antibodies or fragments from the circulation. The chance of side-effects is reduced when chimeric, humanized or human antibodies are administered to humans. In addition generally a longer half-life in the circulation is achieved when chimeric, humanized or human antibodies are used because of reduced clearance when compared to non-human antibodies.

Antibodies specific for a particular antigen, such as FH in accordance with the present invention, can be prepared by various methods known in the art. For instance, human FH can be used as an immunogen for eliciting antibodies. As another example, the CCP17 and/or CCP18 domain of human FH can be used as an immunogen. One example of such method is by immunization and hybridoma generation as described in the Examples. Mouse monoclonal antibodies to FH can for instance be generated by immunizing mice, e.g. BALB/c mice, intraperitoneally with human factor H, optionally in the presence of an adjuvans, such as montanide, for instance at four week intervals. Several days after the fourth immunization, spleen cells can be fused with e.g. the myeloma cell line SP2/0. The presence of factor H specific antibodies in the supernatants of the hybridomas can be tested by ELISA. For instance, microtiterplates are coated with a moAb (e.g. rat anti-mouse kappa moAb RM19) to capture mouse IgG antibodies. Specificity of the antibodies was determined by biotinylated factor H. Another example of a method to provide FH-specific antibodies is by screening phage display libraries expressing recombinant nucleic acid sequences encoding immunoglobulin chains. Methods for antibody phage display have been used in the art and described extensively. Screening of the library for antibodies can be performed with the same antigen used for immunization, e.g. human FH or the CCP17 and/or CCP18 domain of human FH.

Once antibodies or fragments specific for FH, in particular for CCP17 and/or CCP18 of FH, have been obtained, the desired biological activity thereof, i.e. their ability to potentiate the activity of FH, can be tested by several methods known to the skilled person. As described herein before, potentiating the activity of FH preferably encompasses inhibition of hemolytic activity, inhibition of C3 deposition on cells, and/or an increase of binding of FH to C3b. Functional assay's to test these activities are described herein before and detailed in the Examples.

A particularly preferred antibody according to the invention is antibody anti-FH.07, the preparation and identification of which is described in the Examples. Table 1 provides an overview of the variable heavy and light chain sequences, as well as the individual CDR sequences, of antibody anti-FH.07. Even more preferred are monoclonal chimeric or humanized antibodies or fragments thereof comprising the heavy chain CDR sequences and light chain CDR sequences of antibody anti-FH.07 or the heavy chain variable region and the light chain variable region of antibody anti-FH.07. The terms "anti-FH.07" as used herein encompass all antibodies and fragments having at least the heavy chain and light chain CDR1, CDR2 and CDR3 region as depicted in Table 1, such as for instance isolated and/or purified antibodies or recombinantly produced antibodies. Another preferred antibody or fragment according to the invention is an antibody or fragment that competes with antibody anti-FH.07 for binding to FH, in particular to CCP18 of FH. Also provided is therefore an antibody or fragment thereof that specifically binds to CCP17 and/or CCP18, preferably to CCP18, of factor H (FH), that potentiates FH activity, and that competes with antibody anti-FH.07 for binding to FH. Competition can be determined using method well known in the art, for instance by surface plasmon resonance using a Biacore T3000 instrument (GE Healthcare, Little Chalfont, UK), whereby FH is immobilized on a sensor chip and the potentially competing antibodies are flown over the immobilized FH. It is possible to produce an antibody or fragment thereof comprising at least one CDR sequence as depicted in Table 1, which is specific for CC18 of FH, based on the heavy chain and light chain CDR sequences of Table 1.

The invention therefore further provides an isolated, synthetic or recombinant antibody or fragment thereof comprising:

a heavy chain CDR1 sequence of SEQ ID NO:5, and/or
a heavy chain CDR2 sequence of SEQ ID NO:6, and/or
a heavy chain CDR3 sequence of SEQ ID NO:7, and/or
a light chain CDR1 sequence of SEQ ID NO:1, and/or
a light chain CDR2 sequence of SEQ ID NO:2, and/or
a light chain CDR3 sequence of SEQ ID NO:3. Said antibody preferably specifically binds to complement CCP17 and/or CCP18 of FH, more preferably to CCP18, and potentiates FH activity. More preferably, an antibody or fragment according to the invention comprises all three heavy chain CDRs and all three light chain CDR's of Table 1. In one embodiment, an antibody or fragment according to the invention comprises a heavy chain variable region sequence and/or a light chain variable region sequence as depicted in table 1. Also provided is therefore an antibody or fragment according to the invention having a heavy chain sequence of SEQ ID NO:8 and/or having a light chain sequence of SEQ ID NO:4.

Optionally, the sequence of at least one of said CDR is optimized, thereby generating a variant antibody, for instance to improve binding affinity, FH potentiating ability or in vivo or storage stability. In addition, optionally at least one sequence in at least one of the framework regions of an antibody or fragment of the invention is optimized, for instance to improve binding efficacy or stability of the antibody or fragment or to reduce side-effects of non-human sequences after administration thereof to a human. This is for instance done by mutagenesis procedures. A skilled person is capable of generating antibody variants comprising at least one altered CDR or framework sequence. CDR and/or framework sequences are for instance optimized by mutating a nucleic acid molecule encoding such framework sequence. For instance, conservative amino acid substitution is applied. Examples of conservative amino acid substitution include the substitution of one hydrophobic residue such as isoleucine, valine, leucine or methionine for another hydrophobic residue, and the substitution of one polar residue for another polar residue, such as the substitution of arginine for lysine, glutamic acid for aspartic acid, or glutamine for asparagine. In order to select an improved antibody or fragment, the binding affinity, FH potentiating ability and/or stability of the resulting variant antibodies are preferably tested. Preferably, human germline sequences are used for framework regions in antibodies or fragments according to the invention. The use of human germline sequences minimizes the risk of immunogenicity of said antibodies, because these sequences are less likely to contain somatic alterations which are unique to individuals from which the framework regions are derived, and may cause an immunogenic response when applied to another human individual. Typically, up to three amino acid residues of a CDR sequence may vary while retaining the same specificity. Hence, an antibody or fragment according to the invention preferably contains a heavy chain and light chain CDR1, CDR2 and CDR3 sequence wherein at most 3, preferably at most 2, more preferably at most 1 amino acid of each CDR is varied as compared to the heavy and light chain CDR1, CDR2 and CDR3 sequences of Table 1.

The invention therefore further provides an isolated, synthetic or recombinant antibody or fragment thereof comprising:
- a heavy chain CDR1 sequence comprising a sequence which is at least 80% identical to the sequence of SEQ ID NO:5, and/or
- a heavy chain CDR2 sequence comprising a sequence which is at least 80% identical to the sequence of SEQ ID NO:6, and/or
- a heavy chain CDR3 sequence comprising a sequence which is at least 80% identical to the sequence of SEQ ID NO:7, and/or
- a light chain CDR1 sequence comprising a sequence which is at least 80% identical to the sequence of SEQ ID NO:1, and/or
- a light chain CDR2 sequence comprising a sequence which is at least 80% identical to the sequence of SEQ ID NO:2, and/or
- a light chain CDR3 sequence comprising a sequence which is at least 80% identical to the sequence of SEQ ID NO:3. Said antibody preferably specifically binds to complement CCP17 and/or CCP18 of FH, more preferably to CCP18, and potentiates FH activity. Preferably, said antibody or fragment comprises heavy chain CDR1, CDR2 and/or CDR3 sequences and/or light chain CDR1, CDR2 and/or CDR3 sequences that are at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, identical to these sequences.

Further provided is an antibody or fragment according to the invention comprising or having a heavy chain sequence comprising a sequence which has at least 80% sequence identity to the sequence of SEQ ID NO:8 and/or comprising or having a light chain sequence comprising a sequence which has at least 80% sequence identity to the sequence of SEQ ID NO:4, or sequences that are at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, identical to any one of these heavy chain or light chain variable region sequences.

The invention further provides an isolated, synthetic or recombinant nucleic acid molecule comprising a nucleic acid sequence encoding an antibody or fragment thereof according to the invention. Preferred nucleic acid molecules encode at least the heavy chain CDR1, CDR2 and CDR3 and the light chain CDR1, CDR2 and CDR3 as depicted in Table 1. Preferably a nucleic acid molecule according to the invention has a length of at least 30 nucleotides, more preferably at least 50 nucleotides, more preferably at least 75 nucleotides. Preferably, a nucleic acid molecule according to the invention encodes a monoclonal chimeric or humanized antibody or fragment thereof comprising the heavy chain CDR sequences and light chain CDR sequences of antibody anti-FH.07 or the heavy chain variable region and the light chain variable region of antibody anti-FH.07 as depicted in Table 1. Nucleic acid sequences encoding heavy chain and light chain CDR's of antibody anti-FH.07 are depicted in table 1. However, nucleic acid molecules encoding a heavy or a light chain CDR of an antibody according to the invention comprising nucleic acid sequences which differ from the CDR nucleic acid sequences depicted in table 1 but comprising nucleic acid codons encoding the amino acid sequence of said heavy chain or light chain CDR sequence depicted in Table 1 are also encompassed by the invention. Provided is therefore an isolated, synthetic or recombinant nucleic acid molecule comprising a nucleic acid sequence encoding at least the sequences of SEQ ID NO's 1, 2, 3, 5, 6 and 7. Further provided is an isolated, synthetic or recombinant nucleic acid molecule comprising a nucleic acid sequence encoding at least the sequences of SEQ ID NO's 4 and 8. Nucleic acid molecules encoding a heavy and/or light chain CDR or an antibody that is modified for instance by conservative amino acid substitution, are also encompassed by the invention, as long as the encoded CDR amino acid sequence has at least 80% sequence identity with a CDR sequence depicted in table 1, preferably at least 85%, more preferably at least 90%, more preferably at least 95%.

A nucleic acid molecule or nucleic acid sequence according to the invention preferably comprises a chain of nucleotides, more preferably DNA and/or RNA. However, a nucleic acid molecule or nucleic acid sequence of the invention may comprise other kinds of nucleic acid structures such as for instance a DNA/RNA helix, peptide nucleic acid (PNA), locked nucleic acid (LNA) and/or a ribozyme. Such other nucleic acid structures are referred to as functional equivalents of a nucleic acid sequence, and are encompassed by the invention. The term "functional equivalent of a nucleic acid sequence" also encompasses a chain comprising non-natural nucleotides, modified nucleotides and/or non-nucleotide building blocks which exhibit the same function as natural nucleotides.

The invention further provides an isolated, synthetic or recombinant nucleic acid molecule comprising:
- a heavy chain CDR1 sequence comprising a sequence which is at least 80% identical to the sequence of SEQ ID NO:13, and/or
- a heavy chain CDR2 sequence comprising a sequence which is at least 80% identical to the sequence of SEQ ID NO:14, and/or
- a heavy chain CDR3 sequence comprising a sequence which is at least 80% identical to the sequence of SEQ ID NO:15, and/or
- a light chain CDR1 sequence comprising a sequence which is at least 80% identical to the sequence of SEQ ID NO:9, and/or
- a light chain CDR2 sequence comprising a sequence which is at least 80% identical to the sequence of SEQ ID NO:10, and/or
- a light chain CDR3 sequence comprising a sequence which is at least 80% identical to the sequence of SEQ ID NO:11. A nucleic acid molecule according to the invention preferably comprises a sequence which has at least 85%, more preferably at least 90%, more preferably at least 95%, more preferably at least 96%, more preferably at least 97%, more preferably at least 98%, more preferably at least 99% sequence identity to said CDR sequences. Preferably, said nucleic acid molecule comprises a heavy chain sequence comprising a sequence which has at least 80% sequence identity to the sequence of SEQ ID NO:16 and/or comprises a light chain sequence comprising a sequence which has at least 80% sequence identity to the sequence of SEQ ID NO:12, more preferably at least 85%, more preferably at least 90%, more preferably at least 95%, more preferably at least 96%, more preferably at least 97%, more preferably at least 98%, more preferably at least 99% sequence identity to SEQ ID NO:12 and/or SEQ ID NO:16.

The invention further provides a vector comprising a nucleic acid molecule according to the invention. A preferred vector is a plasmid. A "plasmid" is defined herein as a circular, preferably double-stranded, DNA molecule. Methods for preparing a vector comprising a nucleic acid molecule according to the invention are well known in the art. Non-limiting examples of vectors suitable for generating a vector of the invention are retroviral and lentiviral vectors. A vector according to the invention can be used for a variety of applications. A vector according to the invention is preferably used for in vitro expression of a nucleic acid molecule according to the invention in a cell, preferably for the generation of antibodies or fragments according to the invention. Further, a vector according to the invention comprising a nucleic acid molecule according to the invention can be used for therapeutically. Administration of such vector to an individual, preferably a human, in need thereof results in expression of an antibody or fragment according to the invention in vivo.

Further provided is a recombinant cell comprising a nucleic acid molecule or vector according to the invention. Such nucleic acid molecule or vector is for preferably introduced into said cell so that the cell's nucleic acid translation machinery will produce the encoded antibodies or fragments. A nucleic acid molecule or vector according to the invention is preferably expressed in so called producer cells, such as for instance cells of a Chinese hamster ovary (CHO), NSO (a mouse myeloma) or 293(T) cell line, some of which are adapted to commercial antibody production. Proliferation of such producer cells results in a producer cell line capable of producing antibodies or fragments according to the invention. Preferably, said producer cell line is suitable for producing antibodies for use in humans. Hence, said producer cell line is preferably free of pathogenic agents such as pathogenic micro-organisms.

The invention further provides a method for producing an antibody or fragment according to the invention comprising providing a cell with a nucleic acid molecule or a vector according to the invention, and allowing said cell to translate the nucleic acid sequence comprised by said nucleic acid molecule or vector, thereby producing said antibody or fragment according to the invention. A method according to the invention preferably further comprises harvesting, purifying and/or isolating said antibody or fragment. Antibodies or fragments obtained with a method for producing an antibody or fragment according to the invention are also provided.

An antibody or fragment according to the invention can be advantageously used in therapeutic applications. Provided is thus a pharmaceutical composition comprising an antibody or fragment according to the invention and a pharmaceutically acceptable carrier, diluent and/or excipient. Also provided are pharmaceutical compositions comprising a nucleic acid molecule or vector according to the invention and at least one pharmaceutically acceptable carrier, diluent and/or excipient. Non-limiting examples of suitable carriers are for instance keyhole limpet haemocyanin (KLH), serum albumin (e.g. BSA or RSA) and ovalbumin. A preferred carrier is a solution, such as an aqueous solution, for example saline, or an oil-based solution. Non-limiting examples of excipients which can be incorporated in tablets, capsules and the like are a binder such as gum tragacanth, acacia, corn starch or gelatin, an excipient such as microcrystalline cellulose, a disintegrating agent such as corn starch, pregelatinized starch and alginic acid, a lubricant such as magnesium stearate, a sweetening agent such as sucrose, lactose or saccharin, and a flavoring agent such as peppermint, oil of wintergreen or cherry. When the dosage unit form is a capsule, it preferably contains, in addition to one or more of the excipients indicated above, a liquid carrier such as fatty oil. Various other materials may be present as coatings or to modify the physical form of the dosage unit. For instance, tablets may be coated with shellac and/or sugar or both. A pharmaceutical composition according to the invention is preferably suitable for human use.

The pharmaceutical compositions described herein can be administered in a variety of different ways. Examples include administering a pharmaceutical composition comprising an antibody according to the invention and containing a pharmaceutically acceptable carrier via oral, intranasal, rectal, topical, intraperitoneal, intravenous, intramuscular, subcutaneous, subdermal, transdermal, intrathecal, and intracranial methods. For oral administration, the active ingredient can be administered in solid dosage forms, such as capsules, tablets, and powders, or in liquid dosage forms, such as elixirs, syrups, and suspensions. Sterile compositions for injection can be formulated according to conventional pharmaceutical practice by dissolving or suspending the antibody or fragment of the invention in a vehicle for injection, such as water or a naturally occurring oil like sesame oil, coconut oil, peanut oil, cottonseed oil, etc., or a synthetic fatty vehicle like ethyl oleate. Buffers, preservatives and/or antioxidants may also be incorporated.

The invention further provides an antibody or fragment according to the invention for use in therapy. Further provided is a nucleic acid molecule according to the invention for use in therapy. Said therapy can be therapeutic or prophylactic. Antibodies or fragments according to the invention are particularly suitable for the treatment, alleviation or prevention of a disorder associated with alternative pathway complement activation. Provided is therefore an antibody or fragment according to the invention for use in the treatment, alleviation or prevention of a disorder associated with alternative pathway complement activation. Also provided is a nucleic acid molecule according to the invention for use in the treatment, alleviation or prevention of a disorder associated with alternative pathway complement activation. As used herein "a disorder associated with alternative complement activation" is herein defined as a disorder wherein unwanted and/or excessive alternative pathway complement activation leads to cell, tissue or extracellular matrix damage. Cells that may be damaged by unwanted and/or excessive alternative pathway activation are any cell that is in contact with blood, for instance red blood cells, epithelial cells, in particular hepatic and/or kidney epithelial cells, platelets, white blood cells, endothelial cells. Said disorder preferably is a disorder associated with impaired FH function or FH deficiency. More preferably, said disorder is a disorder associated with impaired FH function or FH deficiency but not with FH absence. Since the antibodies and fragments of the invention potentiate the function of FH, the antibodies and fragment are particularly suitable to block or reduce the effects of impaired FH function or FH deficiency. However, as demonstrated in the Examples, the potentiating anti-FH antibodies of the invention not only inhibit lysis of red blood cells that are incubated with serum of patients with compromised alternative pathway activation, but also of red blood cells that are incubated with serum of healthy individuals in which FH is artificially blocked. Hence, antibodies and fragments can also be used to block or reduce unwanted and/or excessive alternative pathway complement activation caused by factors other than impaired FH function or FH deficiency. Non-limiting examples of such orders that can be treated are atypical hemolytic uremic syndrome (aHUS), paroxysmal nocturnal hemoglobinuria (PNH), age-related macular degeneration (AMD), membranoproliferative glomerulonephritis (MPGN).

Atypical hemolytic uremic syndrome (aHUS), also referred to as complement mediated HUS, is characterized by hemolytic anemia, thrombocytopenia, systemic thrombotic microangiopathy (TMA) and renal failure. The onset of aHUS is typically in childhood and episodes of the disease are associated with e.g. infection, pregnancy, other disease, surgery, or trauma. Over 60% of aHUS patients die or develop end stage renal disease (ESRD) despite plasma exchange or plasma supplementation. Several mutations in components or factors of the complement system have been identified in patients with aHUS. Mutations in FH, FI FB, membrane cofactor protein (MCP), thrombomodulin (THBD) or C3 comprise about 50% of the known mutations in patients with aHUS of which mutations of FH are the most frequent (about 20-30% of aHUS patients). The majority of patients are heterozygous for the mutations, which nevertheless results in pathological FH deficiency. In addition, in about 10% of patients aHUS is caused by autoantibodies against FH, also resulting in reduced functional FH. Currently the standard treatment for aHUS is plasma supplementation or plasma exchange therapy. In addition eculizumab is used in the treatment of patients with aHUS. Renal transplantation is associated with a high risk of recurrence which is dependent on the mutation underlying aHUS. Transplantation is contraindicated in children with mutations in FH, FB, FI, C3 or THBD due to the increased risk of recurrence. Antibodies or fragments, preferably comprising at least the Fab fragment, according to the invention are particularly suitable for the treatment, alleviation or prevention of aHUS caused by a mutation in FH or by the presence of anti-FH autoantibodies. However, since the antibodies and fragments of the invention also potentiate the activity of FH in the absence of impaired FH function or FH deficiency, any form of complement dependent aHUS can be advantageously treated, alleviated or prevented with the antibodies or fragments of the invention.

Paroxysmal nocturnal hemoglobinuria (PNH) is caused by a genetic mutation in the X chromosome of a totipotent hematopoietic stem cell. The mutation leads to a deficiency in phosphatidylinositol glycan class A protein, which is critical for the synthesis of glycosylphophatidylinositol membrane anchoring proteins (GPI-AP). Inhibitor of the complement system CD55 is an example of such protein, which binds C3b at the host cell surface thereby preventing the formation of C3 convertase. Hence, a deficiency of these proteins results in unwanted or excessive complement activation. One of the main consequences of PNH is that red blood cells undergo lysis as a result of the excessive activity of the complement system. Recently, eculizumab has been approved for the treatment of PNH in several countries. Other therapies include blood transfusion, erythrocyte-stimulating agent therapy, treatment with corticosteroids and anabolic steroids. Since the antibodies and fragments of the invention preferably also potentiate the activity of FH independent from the levels of FH or FH function, thereby inhibiting the activation of the alternative pathway of the complement system, the antibodies and fragment can be advantageously used in PNH patients. In addition, because the antibodies and fragments of the invention act at the level of C3 deposition, as opposed to eculizumab that acts more downstream of the activation pathways, depletion of cells in the liver is reduced because less cells are opsonized by C3b.

Age-related macular degeneration (AMD) is damage to the retina affects usually affecting older individuals resulting in a loss of vision in the macula, the center of the visual field. Mutations and SNPs (single nucleotide polymorphisms) in FH have recently been implicated in about 35% of AMD patients. The SNP is located in CCP7 of FH and was demonstrated to influence the binding of FH to heparin thereby compromising the ability of FH to bind the host cell surface as well as the extracellular matrix. Antibodies or fragments, preferably comprising at least the Fab fragment, according to the invention are particularly suitable for the treatment, alleviation or prevention AMD characterized by decreased FH function, preferably by a SNP in the gene encoding FH.

Membranoproliferative glomerulonephritis (MPGN) is an uncommon cause of chronic nephritis that occurs primarily in children and young adults. It causes glomerular injury as a result of proliferation of mesangial and endothelial cells and expansion of the mesangial matrix, thickening of the peripheral capillary walls by subendothelial immune deposits and/or intramembranous dense deposits, and mesangial interposition into the capillary wall. MPGN is often associated with a total absence of FH. MPGN that can be treated with antibodies and/or fragments of the inventions is preferably associated with impaired FH function or FH deficiency but not with FH absence. The invention therefore provides an antibody or fragment or nucleic acid molecule for use according to the invention for use in the treatment, alleviation or prevention of a disorder associated with alternative pathway complement activation, wherein said disorder is selected from the group consisting of atypical haemolytic uraemic syndrome (aHUS), paroxysmal nocturnal haemoglobinuria (PNH), age-related macular degeneration (AMD), membranoproliferative glomerulonephritis (MPGN). Also provided is the use of an antibody or fragment, a nucleic acid molecule or a vector according to the invention for the preparation of a medicament for the treatment, alleviation or prevention of a disorder associated with alternative pathway complement activation. Said disorder is preferably selected from the group consisting of atypical haemolytic uraemic syndrome (aHUS), paroxysmal nocturnal haemoglobinuria (PNH), age-related macular degeneration (AMD), membranoproliferative glomerulonephritis (MPGN). Preferred antibodies for use as a medicament or prophylactic agent in accordance with the invention are antibodies or fragments thereof, preferably the Fab, Fab' or $F(ab)_2$ or $F(ab')_2$ fragment, that comprise the heavy and light chain CDR1, CDR2 and CDR3 as depicted in Table 1. Said antibody or fragment is preferably a monoclonal humanized or chimeric antibody or fragment.

The invention further provides a method for inhibiting alternative complement activation comprising administering to an individual an antibody or fragment according to the invention, or a nucleic acid molecule or a vector according to the invention.

The invention further provides a method for treating, alleviating or preventing a disorder associated with alternative pathway complement activation comprising administering to an individual in need thereof a therapeutically effective amount of an antibody or fragment according to the invention. Also provided is a method for treating, alleviating or preventing a disorder associated with alternative pathway complement activation comprising administering to an individual in need thereof a therapeutically effective amount of a nucleic acid molecule or vector according the invention. Further provided is a method for treating, alleviating or preventing a disorder associated with alternative pathway complement activation comprising administering to an individual in need thereof a therapeutically effective amount of a pharmaceutical composition according to the invention. Said disorder is preferably selected from the group consisting of atypical hemolytic uremic syndrome (aHUS), paroxysmal nocturnal hemoglobinuria (PNH), age-related macular degeneration (AMD), membranoproliferative glomerulonephritis (MPGN). As used herein, an "individual" is a human or an animal that has a complement system as part of its immune system, preferably a mammal. In a particularly preferred embodiment the individual is a human. Preferred antibodies for use in the methods of the invention are antibodies or fragments thereof, preferably the Fab, Fab', F(ab)$_2$ or F(ab')$_2$ fragment, that comprise the heavy and light chain CDR1, CDR2 and CDR3 as depicted in Table 1. Said antibody or fragment is preferably a monoclonal humanized or chimeric antibody or fragment.

The compositions containing the antibodies, fragments, nucleic acid molecules of the invention can be administered for prophylactic and/or therapeutic treatments. In therapeutic applications antibodies, fragment, nucleic acid molecules or compositions according to the invention are administered to an individual, preferably a human, already suffering from a disease and/or already showing symptoms of the disease in an amount sufficient to counteract the symptoms of the disease and/or its complications. In prophylactic applications, antibodies, fragment, nucleic acid molecules or compositions according to the invention are administered to an individual, before the individual shows symptoms of the disorder to prevent the development of these symptoms or its complications. For instance, individuals that carry a genetic mutation that may or will cause a disorder associated with alternative complement activation can be prophylactically treated with antibodies, fragment, nucleic acid molecules or compositions according to the invention. The antibodies, fragment, or nucleic acid molecules are typically present in a pharmaceutical composition according to the invention in a therapeutic amount, which is an amount sufficient to remedy a disorder, particularly symptoms associated with a disorder associated with unwanted or excessive activation of the alternative pathway of the complement system.

Features may be described herein as part of the same or separate aspects or embodiments of the present invention for the purpose of clarity and a concise description. It will be appreciated by the skilled person that the scope of the invention may include embodiments having combinations of all or some of the features described herein as part of the same or separate embodiments.

The invention will be explained in more detail in the following, non-limiting examples.

TABLE 1

Amino acid and nucleotide sequences of antibody anti-FH.07 (CDR numbering according to the IMGT numbering system (Lefranc 1997, Lefranc 1999 and Lefranc et al. 2003)

| SEQ ID NO | amino acid/ nucleic acid | Identity | IMGT sequence with indication of amino acid/nucleic acid positions | Sequence |
|---|---|---|---|---|
| 1 | amino acid | Light chain CDR1 (light chain CDR1-IMGT) | SSV.......KY | SSVKY |
| 2 | amino acid | Light chain CDR2 (light chain CDR2-IMGT) | AT.......S | ATS |
| 3 | amino acid | Light chain CDR3 (light chain CDR3-IMGT) | QQWSI....IPPT | QQWSIIPPT |
| 4 | amino acid | Light chain variable region (V-D-J-REGION-IMGT) | QIVLSQSPTFLSASPGEKVTVTCRASSSV.... ...KYMHWYQQKPGASPKPWIFAT....... LASGVP.ARFSGSG..SGTSYSLTISRVEAEDA ATYYCQQWSI....IPPTFGNGTKLELK | QIVLSQSPTFLSASPGEKVTVTCRA SNSSSVKYMHWYQQKPGASPKPWIFAT SNLAAGVPARFSGSGSGTSYSLTIS RVEAEDAATYYCQQWSIIPPTFGNG TKLELK |
| 5 | amino acid | Heavy chain CDR1 (heavy chain CDR1-IMGT) | DFSL....ARYG | DFSLARYG |
| 6 | amino acid | Heavy chain CDR2 (heavy chain CDR2-IMGT) | IWSG...GTA | IWSGGTA |
| 7 | amino acid | Heavy chain CDR3 (heavy chain CDR3-IMGT) | ARNFGN..YAVDY | ARNFGNYAVDY |
| 8 | amino acid | Heavy chain variable region (V-D-J-REGION-IMGT) | QVQLQQSGP.GLVQPSQSLSITCTVSDFSL... .ARYGVHWIRQSPGKGLEWLGVIWSG...GTAD YNAAFI.SRLNINKDNSKSQVFFKMNSLQANDT AIYYCARNFGN..YAVDYWGQGTS | QVQLQQSGPGLVQPSQSLSITCTVS DFSLARYGVHWIRQPGKGLEWLGV IWSGGTADYNAAFISRLNINKDNSK SQVFFKMNSLQANDTAIYYCARNFG NYAVDYWGQGTS |
| 9 | nucleic acid | Light chain CDR1 (light chain CDR1-IMGT) | tcaagtgtc...................aaatac | tcaagtgtcaaatac |

TABLE 1-continued

Amino acid and nucleotide sequences of antibody anti-FH.07 (CDR numbering according to the IMGT numbering system (Lefranc 1997, Lefranc 1999 and Lefranc et al. 2003)

| SEQ ID NO | amino acid/ nucleic acid | Identity | IMGT sequence with indication of amino acid/nucleic acid positions | Sequence |
|---|---|---|---|---|
| 10 | nucleic acid | Light chain CDR2 (light chain CDR2-IMGT) | gccaca.....................tcc | gccacatcc |
| 11 | nucleic acid | Light chain CDR3 (light chain CDR3-IMGT) | cagcagtggagtatt............atccca cccacg | cagcagtggagtattatcccaccca cg |
| 12 | nucleic acid | Light chain variable region (V-D-J-REGION-IMGT) | caaattgttctctcccagtctccaacattcctg tctgcatctccaggtgagaaggtcacagtgact tgcagggccagttcaagtgtc............ .........aaatacatgcactggtatcagcag aaaccaggagcctcccccaaaccctggattttt ggtatcagcagaaaccaggagcctc gccaca.....................tccaac ctggcttctggagtccct...gctcgcttcagt ggcagtggg......tctgggacctcttattct ctcacaatcagcagagtggaggctgaagatgct gccacttattactgccagcagtggagtatt... .........atcccacccacgttcggtaatggg accaagctggagctgaaac | caaattgttctctcccagtctccaa cattcctgtctgcatctccaggtga gaaggtcacagtgacttgcagggcc agtcaagtgtcaaatacatgcact aaaccaggagcctcccccaaaccctggattttt cccaaaccctggattttgccaca tccaacctggcttctggagtccctg ctcgcttcagtggcagtgggtctgg gacctcttattctctcacaatcagc agagtggaggctgaagatgctgcca cttattactgccagcagtggagtat tatcccacccacgttcggtaatggg accaagctggagctgaaac |
| 13 | nucleic acid | Heavy chain CDR1 (heavy chain CDR1-IMGT) | gatttctcatta............gctaggtat ggt | gatttctcattagctaggtatggt |
| 14 | nucleic acid | Heavy chain CDR2 (heavy chain CDR2-IMGT) | atatggagtggt.........ggaaccgca | atatggagtggtggaaccgca |
| 15 | nucleic acid | Heavy chain CDR3 (heavy chain CDR3-IMGT) | gccagaaattttggtaac......tacgctgtg gactac | gccagaaattttggtaactacgctg tggactac |
| 16 | nucleic acid | Heavy chain variable region (V-D-J-REGION-IMGT) | caggtgcagctgcagcagtcaggacct...ggc ctagtgcagccctctcagagcctgtccattacc tgcacagtctctgatttctcatta......... ...gctaggtatggtgtacactggattcgccag tctccaggaaagggtctggagtggctgggagtg atatggagtggt.........ggaaccgcagac tataatgcagctttcata...tccagactgaac atcaacaaggacaattccaagagccaagtttc tttaaaatgaacagtctccaagctaatgacaca gccatatattactgtgccagaaattttggtaac ......tacgctgtggactactgggtcaagga acctcag | caggtgcagctgcagcagtcaggac ctagtgcagccctctcagagcctgtccattacc ctggcctagtgcagccctctcagag tgtccattacctgcacagtctct ...gctaggtatggtgtacactggattcgccag gatttctcattagctaggtatggtg tctccaggaaagggtctggagtggctgggagtg tacactggattcgccagtctccagg atatggagtggtggaaccgcagact ataatgcagctttcatatccagactgaac atcaacaaggacaattccaagagccaagttttc ataatgcagctttcatatccagact tttaaaatgaacagtctccaagctaatgacaca gaacatcaacaaggacaattccaag gccatatattactgtgccagaaattttggtaac agccaagtttctttaaaatgaaca tacgctgtggactactgggtcaagga gtctccaagctaatgacacagcat acctcag atattactgtgccagaaattttggt aactacgctgtggactactgggtc aaggaacctcag |

EXAMPLES

Figure 1:
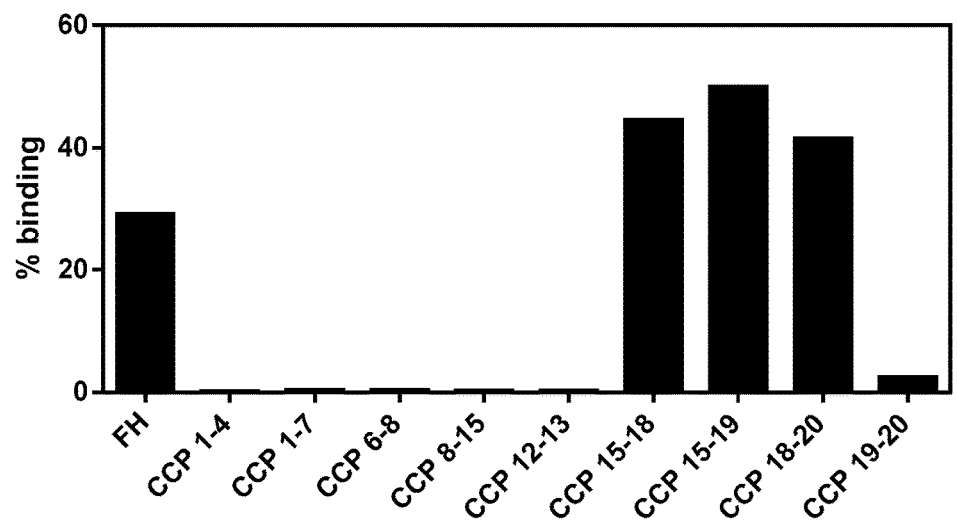
FIG. 1: Characterization of the epitope of monoclonal antibody anti-FH.07. Anti-FH.07 is directed against CCP 18 as indicated by the binding to recombinant FH CCP domains 15-18, 15-19 and 18-20.

Materials and Methods
Reagents

Human purified factor H was obtained from CompTech. (Tyler, Tex. USA). Rat anti-mouse kappa (RM19) was obtained from Sanquin (Business Unit reagents, Sanquin, Amsterdam, the Netherlands). High Performance ELISA buffer (HPE) was obtained from Sanquin. Polyclonal rabbit anti human-factor H was obtained from Sanquin, polyclonal goat anti human FH was obtained from Quidel. Recombinant FH CCPs (CCP 1-4, CCP 1-7, CCP 6-8, CCP 8-15, CCP 12-13, CCP 15-18, CCP 15-19, CCP 18-20 or CCP 19-10) were a kind gift of dr Christoph Schmidt and were produced as described before (Schmidt et al. 2008). Mouse monoclonal antibodies to FH were made as described below. Anti-FH.07 (murine IgG1) is directed against CCP 18, anti-FH.09 (murine IgG1) is directed against CCP 6. Anti-IL-6.8 was use as irrelevant isotype control and was obtained from Sanquin. MoAb anti-C3.19 reacts with an epitope on the C3d fragment of the molecule and has been described before (Wolbink et al. 1993).

Immunization and Hybridoma Generation

Mouse monoclonal antibodies to factor H were generated by immunizing BALB/c mice intraperitoneally with 25 µg human factor H in montanide as adjuvans at four week intervals. Three days after the fourth booster immunization, spleen cells were fused with the myeloma cell line SP2/0. The presence of factor H specific antibodies in the supernatants of the hybridomas was tested by ELISA. In short, microtiterplates were coated with a rat anti-mouse kappa moAb (RM19) to capture mouse IgG antibodies. Specificity of the antibodies was determined by biotinylated factor H. The assay was developed with streptavidin-HRP and TMB.

Epitope Mapping moAbs

Reactivity of FH specific moAbs was tested with recombinant human FH fragments composed of multiple CCPs. To this end, fifty microliter of 100 µg/ml anti-FH moAbs was mixed with 0.5 ml of 2 mg/ml RM-19 coupled-sepharose (25 µg moAb per 1 mg CnBr-Sepharose). The FH fragments were labelled with $^{125}$I and 100 µl (20000c/30 sec) was added to each sample followed by incubation O/N. The assay was performed in PBS with 0.1% (w/v) Tween-20 and 0.1% (w/v) BSA (PTB). Samples were washed 5 times with PBS with 0.1% (w/v) Tween-20 and counted for 30 seconds. Sepharose bound radioactivity was measured and compared to total input (set to 100%).

Generation of F(ab')$_2$ and Fab' Fragments of Monoclonal Antibodies

To make F(ab')$_2$ fragments of the anti-FH moAbs 5.2 mg of each antibody in 5.2 ml 0.1 M citric acid/trisodium citratebuffer, pH 3.7, were incubated with pepsin (20 µg/ml) (Sigma P-6887) for 16 hrs at 37° C. Next, 3 M sodiumchloride and 1 M TRIS were added and the pH was adjusted to 8.9. A protA sepharose column was used to remove remaining intact antibodies and/or Fc fragments. To make monovalent Fab' fragments, the F(ab')$_2$ fragments were reduced by incubation with 10 mM dithioerythritol for 60 min. Subsequently free thiol groups were blocked with 20 mM Iodoacetamide. Fragments were dialyzed to PBS and cleavage efficiency was checked on SDS-PAGE.

SRBC Hemolytic Assay

Factor H functionality was measured with the use of a hemolytic assay as previously described by Sanchez-Corral et al. (2004) and Wouters et al. (2008) with some adjustments. Sheep red blood cells (SRBCs) were diluted in veronal buffer (3 mM barbital, 1.8 mM sodium barbital, 145 NaCl, pH 7.4 (VB)) supplemented with 5.8% (w/v) sucrose (VBS) to a final concentration of $2.1*10^8$ cells/ml. Normal pooled human serum or aHUS patient serum was diluted to 20% (v/v) in veronal buffer containing 0.05% (w/v) gelatine, 10 mM MgCl2, 20 mM EGTA (VBG-AP) with or without addition of the indicated anti-FH moAbs at appropriate concentrations. The assay was performed by mixing 50 µl of serum sample with 50 µl SRBCs suspension to reach a final concentration of 10% (v/v) serum with $1.05*10^8$ cells/ml in 5 mM MgCl2, 10 mM EGTA followed by incubating at 37° C. for 1.25 hours while shaking at 200 rpm. The lysis was stopped by addition of 100 µl ice-cold VB containing 20 mM EDTA followed by centrifugation in a pre-chilled centrifuge (7° C.) at 1800 rpm for 2.5 minutes. The absorbance of the supernatants was measured at 412 nm on a Synergy 2 Microplate Reader (BioTek). The lysis of each sample was expressed as percentage compared to the 100% lysis control (SRBCs incubated in $H_2O$ with 0.6% (w/v) Saponin). As negative control, SRBCs were incubated with serum diluted in VB supplemented with 10 mM EDTA to prevent complement activation.

C3 Deposition on Zymosan and LPS

Microtiterplates were coated with either zymosan (100 µg/ml in PBS coated o/n at RT on Nunc polysorp 96-wells microtiterplates) or Salmonella typhosa LPS (Sigma L-6386, 40 µg/ml in PBS coated O/N at RT on Nunc polysorp 96-wells microtiterplates). After washing with PBS/Tween human healthy donor serum was incubated in Veronalbuffer containing 0.05% (w/v) gelatin, 5 mM MgCl2, 10 mM EGTA and 0.1% (w/v) Tween-20 in the presence or absence of anti-FH moAbs or antibody fragments at indicated concentrations. C3 deposition was detected with biotinylated moAb anti-C3.19 (0.55 µg/ml in HPE) followed by incubation with 0.01% (v/v) Streptavidin conjugated with poly-HRP, in HPE.

Factor H Binding to C3b

C3b was coated o/n on a microtiter ELISA plate (40 µg/ml in carbonate-bicarbonate buffer, pH 9.6). Healthy donor serum (diluted 1:8 in PBS/BSA/poloxamer/EDTA) was pre-incubated with anti-FH moAbs (100 µg/ml) for 2.5 hrs at RT before incubation on the C3b coated plate. Bound FH was detected with peroxidase-labeled polyclonal goat anti-FH.ELISA (1 µg/ml) was developed with TMB.

SPR Analysis of FH Interactions with C3b, iC3b and C3d

Binding of FH to C3b, iC3b or C3d in the presence of the anti-FH moAbs was determined by surface plasmon resonance using a Biacore T3000 instrument (GE Healthcare, Little Chalfont, UK). Purified C3b, iC3b or C3d (Complement Technologies) was immobilized onto one of three flow cells of a CM5 Biacore Sensor Chip (GE Healthcare) using standard amine coupling. The remaining flow cell was used as reference surface and prepared by performing a coupling reaction without the addition of any protein. A response of 4400 response units (RUs), 4180 RUs and 1470 RUs was obtained after coupling with C3b, iC3b and C3d, respectively. SPR experiments were performed at 25° C. using a flow rate of 10 µl/min and in 10 mM HEPES-buffered 150 mM saline, pH 7.4, with 0.05% (w/v) Tween-20 (HBS-P). Duplicate injections of 0.5 µM FH with a contact time of 210 seconds were performed to obtain a reference binding signal for FH on each surface. After each sample injection a dissociationtime of 240 seconds was allowed, using HBS-P as running buffer, followed by a single 30 seconds injection of 1 M NaCl to regenerate the surface.

To determine the effect of anti-FH.07 without interference of possible cross-linking via the moAb, Fab' fragments, generated as described above, were used. Fab' fragments were mixed with 0.5 µM purified FH in a 2 to 1 molar ratio and each Fab' fragment was also injected without addition of FH to determine any interactions of the Fab' fragments with the surfaces.

Results

Monoclonal Antibodies

We obtained 21 monoclonal antibodies against human FH. MoAbs were numbered following the order of identification. All antibodies were able to capture soluble human FH, indicating a high affinity Some moAbs inhibit cofactor activity by blocking the interaction with factor I and other moAbs inhibit binding of FH to cell surfaces as indicated by enhanced SRBC lysis upon incubation with normal human serum. One of the latter inhibiting moAbs (anti-FH.09) was used in the Examples to induce in vitro lysis of SRBC upon incubation with normal human serum. Anti-FH.03 did not inhibit FH and was used in the Examples as a control antibody. In addition to inhibiting moAbs we identified one moAb (anti-FH.07) that enhanced the function of FH.

Mapping Binding Sites of moAbs by Use of Recombinant FH Fragments

In order to map the binding site of anti-FH.07, we tested the reactivity of this moAb towards a panel of radiolabeled recombinant CCP domains or purified human FH. Binding of the moAbs was tested in a radioimmunoassay and was related to the input (100%). As indicated in FIG. 1, anti-FH.07 binds to recombinant fragments CCP 15-18, CCP 15-19 and CCP 18-20, indicating that anti-FH.07 is specific for CCP 18 of the FH molecule.

Anti-FH.07 Inhibits SRBC Lysis that was Induced by a Blocking Anti-FH moAb

Figure 2:
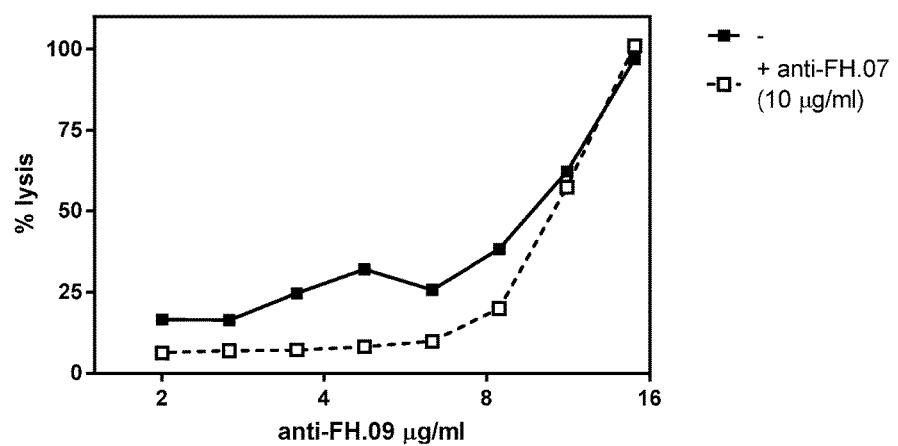
FIG. 2: Anti-FH.07 inhibits SRBC lysis that was induced by moAb anti-FH.09 (blocking moAb against CCP 6) in healthy donor serum. A. Titration of anti-FH.09 to induce SRBC lysis, inhibited by a fixed amount of anti-FH.07 (500 nM). B. Fixed amount of anti-FH.09 (8.5 µg/ml) to induce suboptimal lysis, inhibited by increasing amounts of anti-FH.07.
Figure 2:
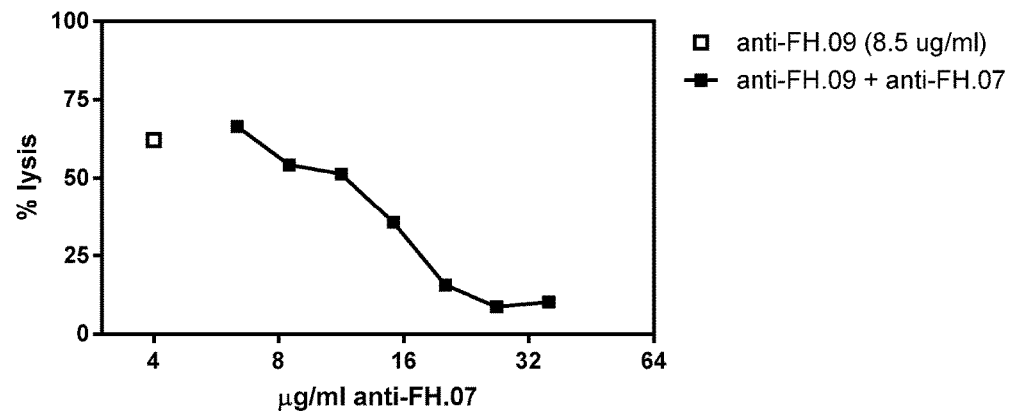

To investigate the effect of anti-FH.07 on the function of factor H, we first induced lysis of SRBCs by a blocking antibody against FH (anti-FH.09). Under normal conditions, incubation of SRBC with healthy human donor serum does not lead to lysis of SRBCs, because these cells are protected by factor H in the serum that binds to sialic acid on the SRBC surface. Upon incubation of normal human serum with increasing amounts of blocking moAb anti-FH.09, dose-dependent lysis of SRBC was observed (FIG. 2A). This can be explained by insufficient protection of the cell surface by serum FH. When a fixed amount of anti-FH.07 was added, the SRBC lysis was inhibited. This indicates that anti-FH.07 is counteracting the effect of anti-FH.09 (FIG. 2A).

In an additional experiment, a fixed amount of anti-FH.09 was added to healthy donor serum to induce suboptimal lysis (approximately 60%) of SRBCs. By addition of increasing amounts of anti-FH.07 this lysis could be completely blocked (FIG. 2B), again showing opposite effects of these monoclonal antibodies.

Anti-FH.07 Inhibits Alternative Pathway Mediated C3 Deposition on Zymosan and LPS To investigate whether anti-FH.07 has an effect on alternative pathway inhibition by FH and to exclude a direct effect on SRBCs or on lysis of these cells, a C3 deposition assay on zymosan or LPS as alternative pathway activators was performed. The experiments were performed in MgEGTA veronal buffer to exclude the Ca2+ dependent classical or lectin pathway activation.

Figure 3:
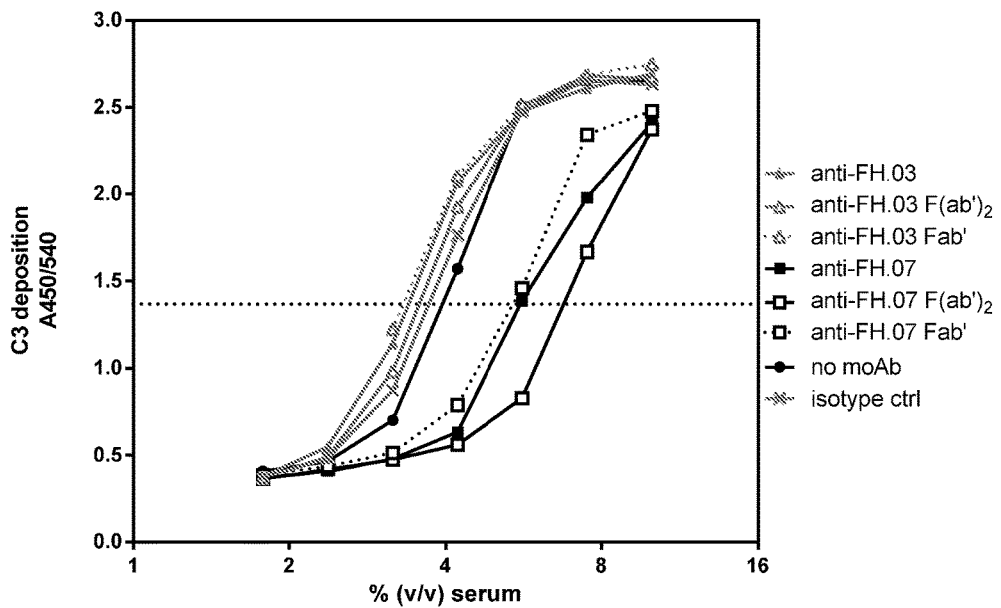
FIG. 3: A,B. Anti-FH.07 and F(ab')₂ and Fab' fragments thereof inhibit alternative pathway activation, as measured by C3 deposition, on zymosan and LPS coat. A. Serum titration on zymosan, fixed amount of anti-FH.07 (intact, F(ab')₂, Fab', 500 nM). B. Fixed serum dilution on LPS, titration of anti-FH.07 (intact, F(ab')₂, Fab'). C. Crosslinking of FH determined in a bridging ELISA. Fab' cannot crosslink FH.
Figure 3:
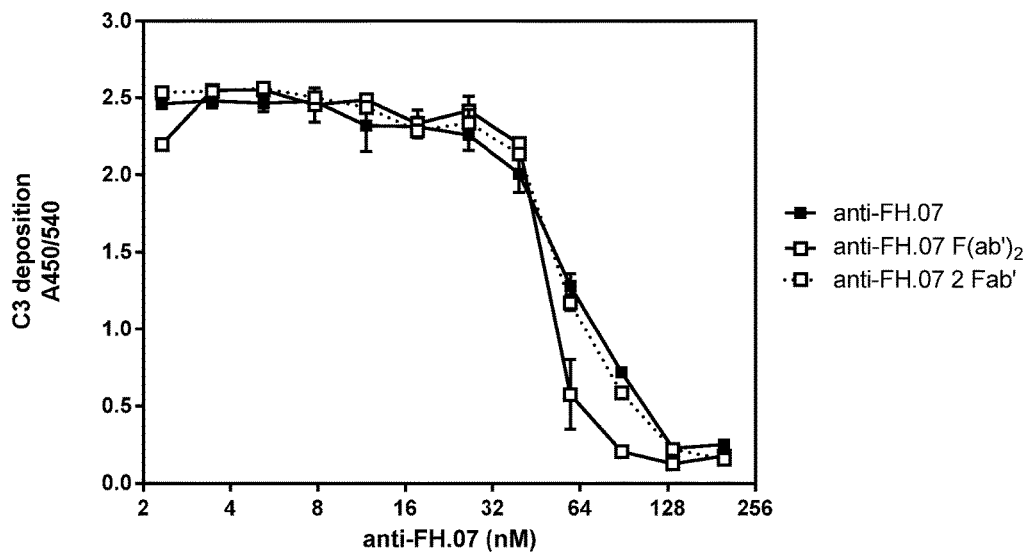
Figure 3:
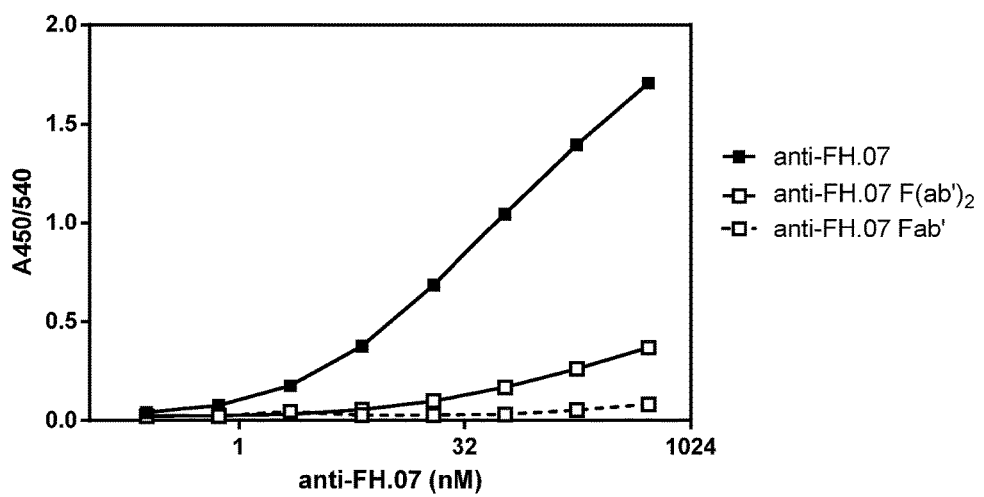

Incubation of increasing serum concentrations on either zymosan or LPS coated plates resulted in dose dependent C3 deposition. By adding a fixed amount of anti-FH.07 (500 nM) to a serum titration, C3 deposition was inhibited (FIG. 3A), indicated by a shifted curve to the right. This shift was not observed when adding the same amount of anti-FH.03, a non-inhibiting anti-FH moAb, to serum. This indicates that the inhibitory function of FH on alternative pathway activation is strengthened by the addition of anti-FH.07. Additionally, by adding increasing amounts of anti-FH.07 to a fixed serum concentration (1:10) on a LPS coated plate, C3 deposition could be completely blocked (FIG. 3B).

Fab' Fragments of Anti-FH.07 have the Same Effect as the Intact moAb

One possible mechanism for the observed increased FH inhibitory function upon incubation with anti-FH.07 is multimerization of FH by crosslinking via the antibody, thereby increasing the avidity of FH for the surface. To test this possibility, we generated monovalent Fab' fragments of anti-FH.07. If crosslinking of FH is the cause of the observed increased FH function, monovalent Fab' fragments are expected to show no potentiating effect. With a bridging ELISA we first checked whether the generated Fab' fragments were indeed completely monovalent and not capable to crosslink FH molecules. To this end an ELISA plate was coated with FH and biotinylated FH was used for detection. As indicated in FIG. 3C, the generated Fab' fragments were unable to crosslink FH on the coat and FH in the fluid phase, while F(ab')$_2$ fragments and intact IgG were able to do so. The anti-FH.07 F(ab')$_2$ and Fab' fragments were then tested in the C3 deposition assays on zymosan and LPS coated plates. To our surprise we observed the same potentiating effect of the Fab' fragments on FH function. Anti-FH.07 Fab' fragments resulted in the same decreased C3 deposition as the intact IgG antibody, both on zymosan and LPS (FIGS. 3A and 3B). Therefore we concluded that the effect of anti-FH.07 was not due to crosslinking of FH molecules by the monoclonal antibody. Moreover, this is underlined by the fact that we did not observe any potentiating effect of any other of the 20 monoclonal Abs in our panel.

Anti-FH.07 Restores FH Protective Function in aHUS Patient Sera

Figure 4:
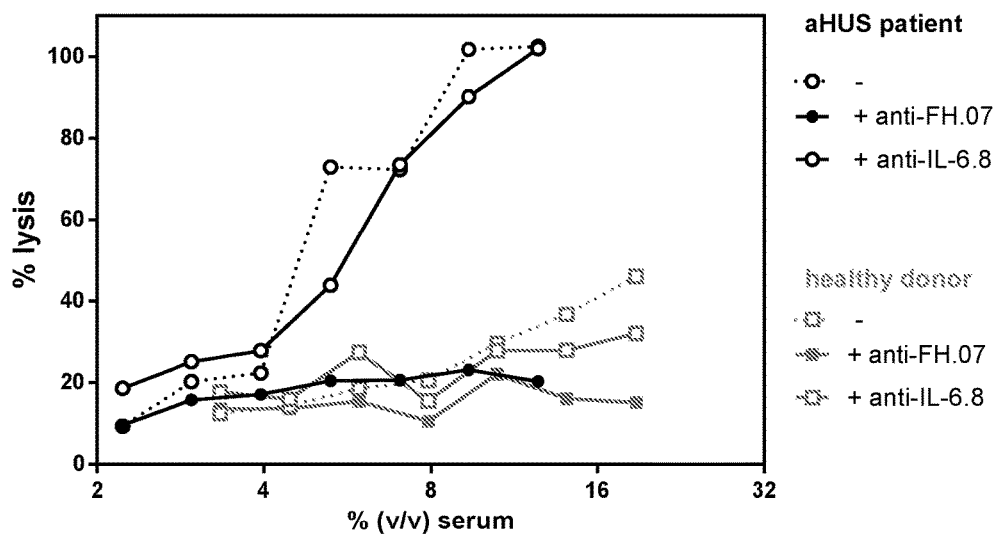
FIG. 4: SRBC lysis because of insufficient functional FH in aHUS patients sera can be inhibited by anti-FH.07 (either intact, F(ab')₂ or Fab' fragments). B,C. 10% (v/v) serum in MgEGTA+100 µg/ml intact antibody, F(ab')₂ or Fab' fragments.
Figure 4:
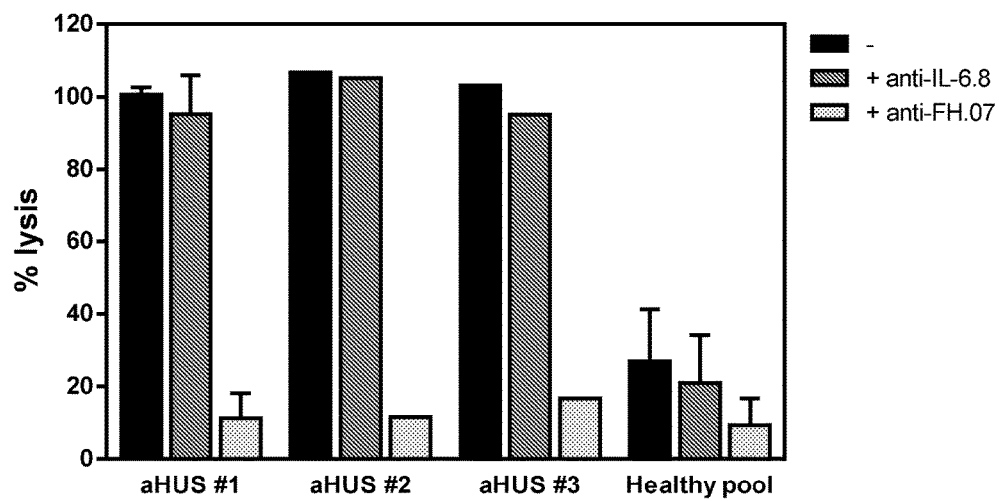
Figure 4:
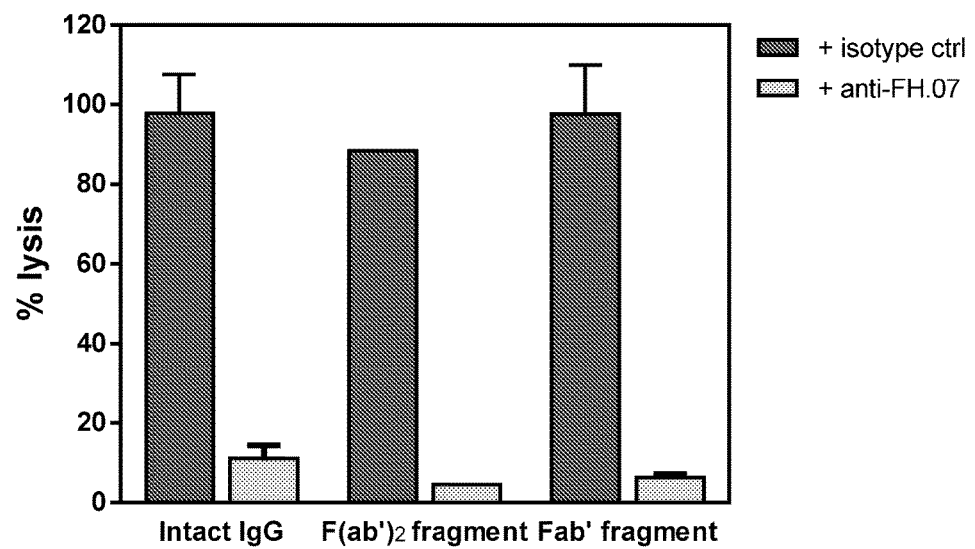

Incubation of SRBCs with increasing amounts of serum of an aHUS patient with a known mutation in CCP 20 leads to lysis of the cells due to insufficient protection of the cells against complement activation (FIG. 4A). However, approximately half the FH in this patient serum is functional, since this patient (as most aHUS patients) has a heterozygous mutation. Based on the previous results, we hypothesized that pre-incubation of aHUS patient serum with anti-FH.07 would lead to potentiation of FH function, resulting in restored protection of SRBCs. Indeed, when we incubated aHUS patient serum with anti-FH.07, the observed lysis of SRBCs was completely abrogated (FIGS. 4A and 4B), while control antibodies showed no effect. This result was obtained in three unrelated aHUS patients which all carry an unique heterozygous mutation in SCR 20 of FH (FIG. 4B). In line with the C3 deposition experiments on zymosan and LPS as described above, also F(ab')$_2$ and Fab' fragments of anti-FH.07 could inhibit complement mediated SRBC lysis in this patient serum (FIG. 4C).

Factor H Binding to C3b Increased in the Presence of Anti-FH.07

Figure 5:
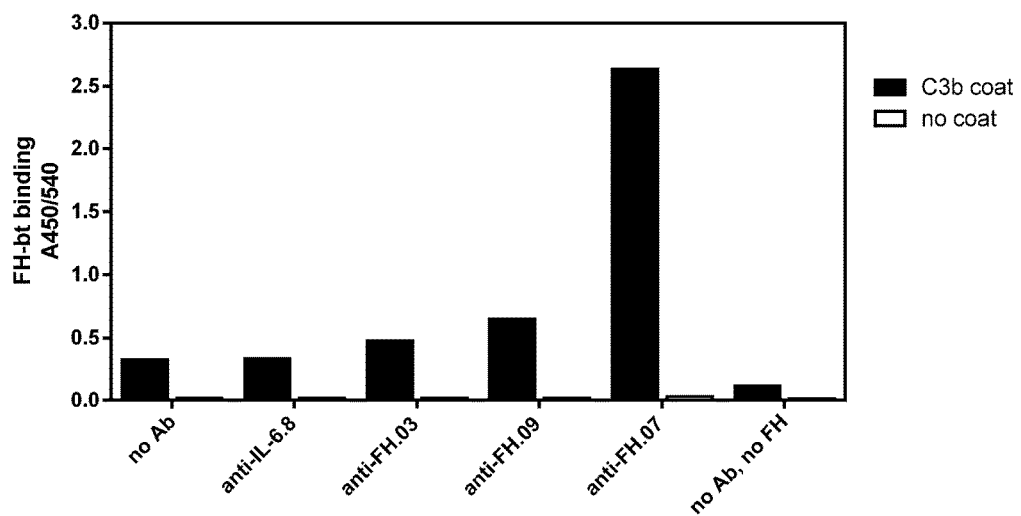
FIG. 5: A. Anti-FH.07 increases binding of FH to C3b as measured by ELISA. B, C, D. Sensograms of SPR analysis of FH interactions with (B) C3b, (C) iC3b, and (D) C3d. Addition of anti-FH.07 Fab' fragments increased the measured RU by at least 2-fold on all surfaces, reflecting increased FH binding.
Figure 5:
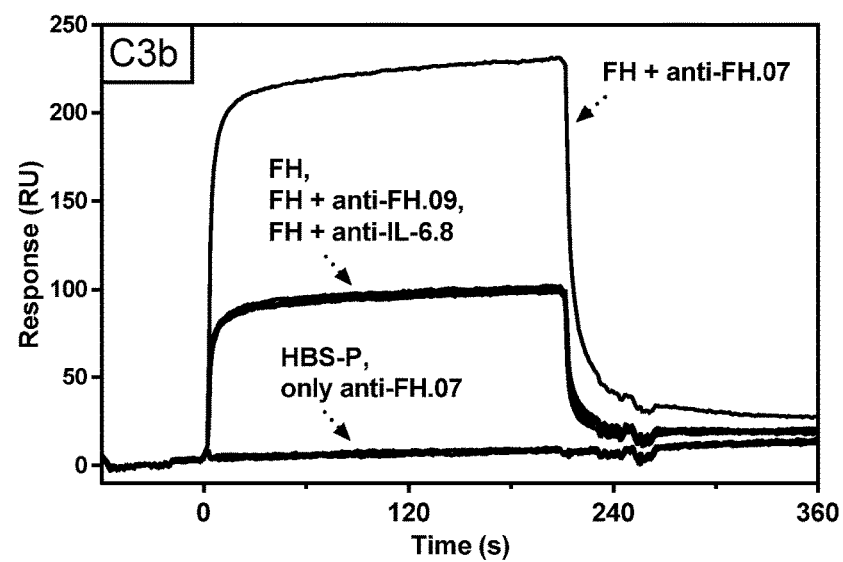
Figure 5:
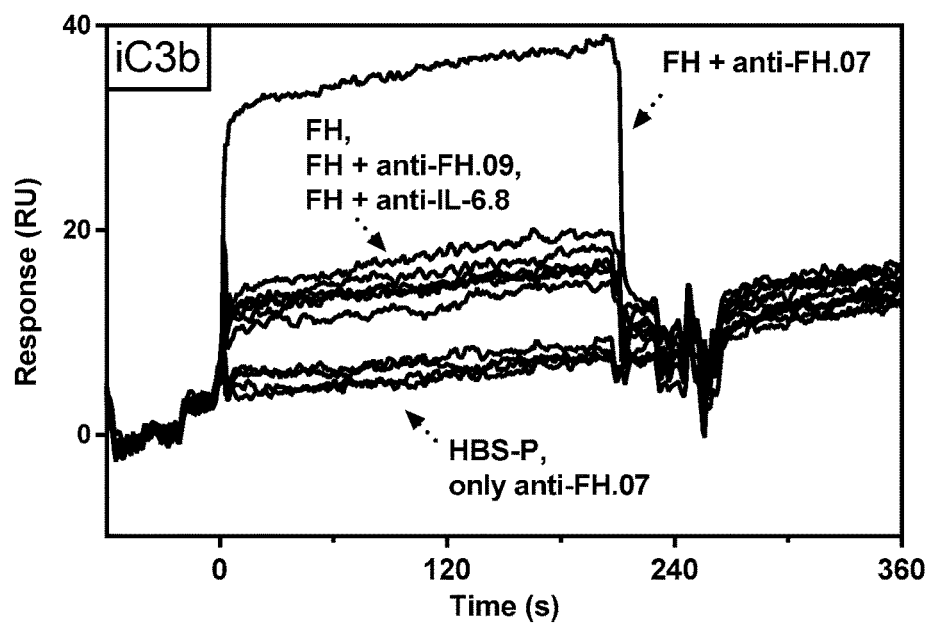
Figure 5:
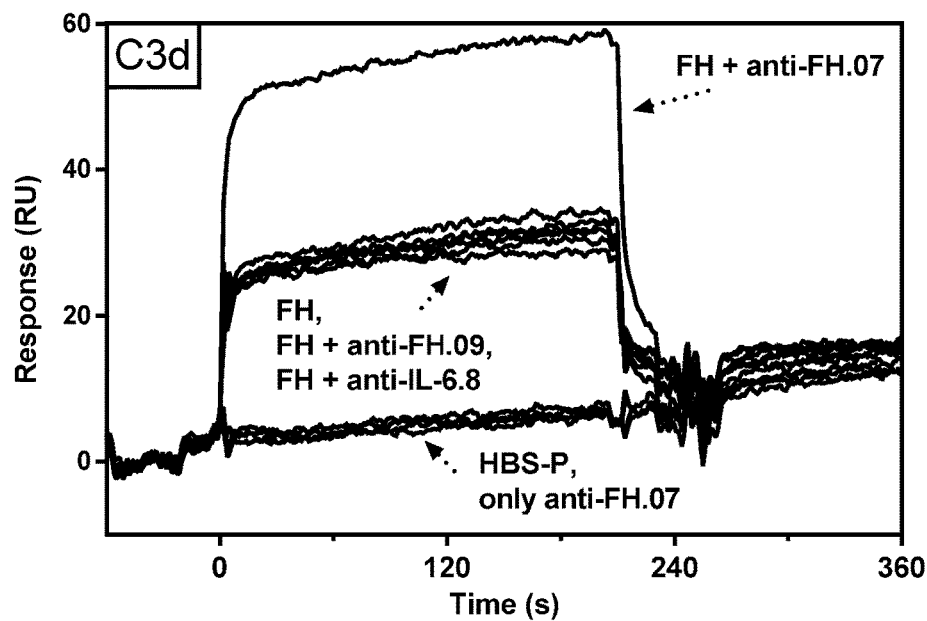

Since Fab' fragments of anti-FH.07 exert the same potentiating effect on FH function as intact IgG, multimerization of FH molecules by the monoclonal antibody cannot be the explanation for the potentiation. We hypothesized that perhaps by binding of anti-FH.07 to CCP 18, the conformation of FH changes in such a way that binding to surfaces is increased. Factor H has binding sites for both C3b and glycosaminoglycans, located at different sites throughout the molecule. Since we observed the FH potentiating effect on C3 deposition on zymosan and LPS, we first studied the effect of anti-FH.07 on FH binding to C3b. To this end, an ELISA plate was coated with C3b and bound FH from normal human serum was detected with HRP labeled polyclonal anti-FH. As shown in FIG. 5, anti-FH.07 significantly increased the binding of FH to C3b, while other anti-FH moAbs (irrelevant moAb or other FH specific antibodies without potentiating effect) had no effect.

In addition, SPR experiments were conducted to study the interaction of FH with C3b, iC3b and C3d in the absence and presence of anti-FH.07 Fab' fragments. Briefly, three flow cells of a CM5 Biacore Sensor chip were coated with either C3b, iC3b or C3d and interactions of FH with these surfaces in the absence or presence of anti-FH moAb was determined on a Biacore T3000 system.

Under normal conditions FH shows interactions with C3b and relatively little interactions with iC3b and C3d. Addition of Fab' fragments of anti-FH.09 or the isotype control (anti-IL-6.8) did not affect binding of FH to C3b, iC3b or C3d. However, addition of Fab' fragments of anti-FH.07 greatly increased the response on the C3b coated surface (FIG. 5B). Anti-FH.07 itself did not show any interactions with C3b, indicating that the increased response measured was caused by increased binding of FH to each of the surfaces. Even the binding to iC3b and C3d, which is normally low for native FH, increased after addition of anti-FH.07 (FIGS. 5C and 5D, respectively). The measured interactions increased at least 2-fold on all surfaces and thereby could not be merely explained by the 33% expected increase in mass of FH after binding of an anti-FH moAb Fab' fragment.

This patent application includes a sequence listing in computer readable format which file is named Stichting0451331.txt created Aug. 9, 2017, and having a size of 8,192 bytes, which sequence listing in incorporated herein by reference.

REFERENCES

Cheng Z Z, Corey M J, Parepalo M, Majno S, Hellwage J, Zipfel P F, Kinders R J, Raitanen M, Meri S, Jokiranta T S. Complement factor H as a marker for detection of bladder cancer. Clin Chem. 2005; 51(5):856-63.

Corey M J, Kinders R J, Poduje C M, Bruce C L, Rowley H, Brown L G, Hass G M, Vessella R L. Mechanistic studies of the effects of anti-factor H antibodies on complement-mediated lysis. J Biol Chem. 2000; 275(17): 12917-25.

Lefranc M P, "Unique database numbering system for immunogenetic analysis" Immunology Today, 18, 509 (1997). PMID: 9386342.

Lefranc M P, "The IMGT unique numbering for immunoglobulins, T cell Receptors and Ig-like domains", The Immunologist. 1999; 7, 132-136.

Lefranc M P, Pommié C, Ruiz M, Giudicelli V, Foulquier E, Truong L, Thouvenin-Contet V, and Lefranc G, "IMGT unique numbering for immunoglobulin and T cell receptor variable domains and Ig superfamily V-like domains" Dev. Comp. Immunol., 27, 55-77 (2003). PMID 12477501.

Sanchez-Corral P, Gonzalez-Rubio C, Rodriguez de Cordoba S, Lopez-Trascasa M. Functional analysis in serum from atypical Hemolytic Uremic Syndrome patients reveals impaired protection of host cells associated with mutations in factor H. Mol Immunol, 2004 May; 41(1): 81-4.

Schmidt C Q, Herbert A P, Kavanagh D, Gandy C, Fenton C J, Blaum B S, Lyon M, Uhrin D, Barlow P N. A new map of glycosaminoglycan and C3b binding sites on factor H. J Immunol, 2008 Aug. 15; 181(4):2610-9.

Wouters D, Brouwer M C, Daha M R, Hack C E. Studies on the haemolytic activity of circulating C1q-C3/C4 complexes. Mol Immunol, 2008 April; 45(7):1893-9. Epub 2007 Dec. 3.

Wolbink G J, Bollen J, Baars J W, ten Berge R J, Swaak A J, Paardekooper J, Hack C E. Application of a monoclonal antibody against a neoepitope on activated C4 in an ELISA for the quantification of complement activation via the classical pathway J Immunol Methods, 1993 Jul. 6; 163(1):67-76.

The invention claimed is:

1. An isolated, synthetic or recombinant antibody or fragment thereof that specifically binds to complement control protein domain 18 (CCP18) of factor H (FH), the antibody or fragment comprising:
   (a) a heavy chain CDR1 having the sequence of SEQ ID NO:5, a heavy chain CDR2 having the sequence of SEQ ID NO:6 and a heavy chain CDR3 sequence having the sequence of SEQ ID NO:7, or
   (b) a light chain CDR1 sequence having the sequence of SEQ ID NO:1, a light chain CDR2 sequence having the sequence of SEQ ID NO:2 and a light chain CDR3 having the sequence of SEQ ID NO:3.

2. The antibody or fragment according to claim 1, wherein the antibody or fragment inhibits alternative complement activation wherein the inhibition comprises:
   (i) inhibition of hemolytic activity,
   (ii) an inhibition of complement component 3 (C3) deposition on cells of said individual, or
   (ii) an increase of binding of FH to C3b, iC3b and/or C3d.

3. The antibody or fragment of claim 1, wherein said fragment comprises a Fab fragment.

4. The antibody of claim 1, wherein the antibody is a monoclonal antibody or fragment thereof.

5. The antibody or fragment according to claim 1, wherein the antibody is a chimeric or humanized antibody, or fragment thereof.

6. The antibody or fragment according to claim 1 comprising a heavy chain sequence comprising a sequence which has at least 80% sequence identity to the sequence of SEQ ID NO:8 or a light chain sequence comprising a sequence which has at least 80% sequence identity to the sequence of SEQ ID NO:4.

7. An isolated, synthetic or recombinant nucleic acid molecule comprising a nucleic acid sequence encoding the antibody or fragment according to claim 1.

8. The nucleic acid molecule according to claim 7 comprising:
   a heavy chain CDR1 sequence comprising a sequence which is at least 80% identical to the sequence of SEQ ID NO:13,
   a heavy chain CDR2 sequence comprising a sequence which is at least 80% identical to the sequence of SEQ ID NO:14,
   a heavy chain CDR3 sequence comprising a sequence which is at least 80% identical to the sequence of SEQ ID NO:15,
   a light chain CDR1 sequence comprising a sequence which is at least 80% identical to the sequence of SEQ ID NO:9,
   a light chain CDR2 sequence comprising a sequence which is at least 80% identical to the sequence of SEQ ID NO:10, or
   a light chain CDR3 sequence comprising a sequence which is at least 80% identical to the sequence of SEQ ID NO:11.

9. The nucleic acid molecule according to claim 7 comprising a heavy chain sequence comprising a sequence which has at least 80% sequence identity to the sequence of SEQ ID NO:16 or comprising a light chain sequence comprising a sequence which has at least 80% sequence identity to the sequence of SEQ ID NO:12.

10. A vector or recombinant cell comprising a nucleic acid molecule according to claim 7.

11. A pharmaceutical composition comprising (i) the antibody or fragment of claim 1, or (ii) a nucleic acid molecule comprising a nucleic acid sequence encoding the antibody or fragment of claim 1, or (iii) a vector comprising the nucleic acid molecule of (ii), and a pharmaceutically acceptable carrier, diluent and/or excipient.

12. A method for treating or alleviating a disorder associated with alternative pathway complement activation comprising administering to an individual in need thereof a therapeutically effective amount of the antibody or fragment according to claim 1.

13. A method according to claim 12, wherein said disorder is selected from the group consisting of atypical hemolytic uremic syndrome (aHUS), paroxysmal nocturnal hemoglobinuria (PNH), age-related macular degeneration (AMD) membranoproliferative glomerulonephritis (MPGN).

14. A method for inhibiting alternative complement activation comprising administering to an individual the antibody or fragment according to claim 1.

15. A method for producing an antibody or fragment according to claim 1, the method comprising introducing into a cell a nucleic acid molecule comprising a nucleic acid sequence encoding the antibody or fragment or a vector comprising the nucleic acid molecule, and allowing said cell to translate the nucleic acid sequence comprised by said nucleic acid molecule or vector, thereby producing said antibody or fragment according to claim 1.

16. A method according to claim 15 further comprising harvesting, purifying and/or isolating said antibody or fragment according to claim 1.

* * * * *

UNITED STATES PATENT AND TRADEMARK OFFICE
CERTIFICATE OF CORRECTION

| | | |
|---|---|---|
| PATENT NO. | : 10,112,993 B2 | Page 1 of 1 |
| APPLICATION NO. | : 15/504983 | |
| DATED | : October 30, 2018 | |
| INVENTOR(S) | : Taco Willem Kuijpers et al. | |

It is certified that error appears in the above-identified patent and that said Letters Patent is hereby corrected as shown below:

In the Specification

In Column 1, Line 12. add new paragraph -- The instant application contains a Sequence Listing which has been submitted electronically in ASCII format and is hereby incorporated by reference in its entirety. Said ASCII copy, created on April 15, 2019, is named SUBseqlist_ST25_4-8-2019-0451331.txt and is 6,037 bytes in size. --

Signed and Sealed this
Twenty-third Day of July, 2019

Andrei Iancu
*Director of the United States Patent and Trademark Office*